(12) United States Patent
Hernandez et al.

(10) Patent No.: US 12,133,644 B2
(45) Date of Patent: Nov. 5, 2024

(54) KNOTLESS INSTABILITY DEVICES AND METHODS FOR SOFT TISSUE REPAIR

(71) Applicant: Medos International Sàrl, Le Locle (CH)

(72) Inventors: Joseph Hernandez, Rutland, MA (US); Gerome Miller, Randolph, MA (US); Mehmet Ziya Sengun, Canton, MA (US); Erik Sojka, Dighton, MA (US); Gregory R. Whittaker, Stoneham, MA (US)

(73) Assignee: Medos International Sarl, Le Locle (CH)

( * ) Notice: Subject to any disclaimer, the term of this patent is extended or adjusted under 35 U.S.C. 154(b) by 807 days.

(21) Appl. No.: 17/180,102

(22) Filed: Feb. 19, 2021

(65) Prior Publication Data

US 2022/0265261 A1    Aug. 25, 2022

(51) Int. Cl.
*A61B 17/04* (2006.01)

(52) U.S. Cl.
CPC .. *A61B 17/0401* (2013.01); *A61B 2017/0414* (2013.01); *A61B 2017/0445* (2013.01)

(58) Field of Classification Search
CPC ........ A61B 17/0401; A61B 2017/0403; A61B 2017/0404; A61B 2017/0406; A61B 2017/0408; A61B 2017/0412; A61B 2017/0414; A61B 2017/0427; A61B 2017/044; A61B 2017/0445; A61B 2017/0446; A61B 2017/0456; A61B 2017/0458; A61B 2017/0459; A61B 2017/0464
See application file for complete search history.

(56) References Cited

U.S. PATENT DOCUMENTS

| | | | |
|---|---|---|---|
| 2,115,636 A | 4/1938 | Kinnear et al. |
| 5,690,676 A | 11/1997 | DiPoto et al. |
| 5,904,704 A | 5/1999 | Goble et al. |
| 6,508,830 B2 | 1/2003 | Steiner |
| 6,544,281 B2 | 4/2003 | ElAttrache et al. |

(Continued)

OTHER PUBLICATIONS

European Search Report for Application No. 22157542.6 issued Jul. 27, 2022 (14 pages).

(Continued)

*Primary Examiner* — Dianne Dornbusch
(74) *Attorney, Agent, or Firm* — Barnes & Thornburg LLP

(57) ABSTRACT

Knotless suture anchors and methods are provided for affixing soft tissue to a bone. One exemplary embodiment of a suture anchor includes an insertion rod, a distal tip member removably coupled to a distal end of the insertion rod, the distal tip member having a suture engagement feature configured to have a plurality of suture limbs slidably coupled to the tip member, and a proximal main member having an elongated cylindrical body with one or more bone-engaging features disposed on its outer surface and a longitudinal lumen extending from a proximal end to a distal end. The suture anchor can also include two suture limb holding surfaces to maintain two suture limbs a distance apart from each other. Other exemplary embodiments, as well as methods for affixing soft tissue to a bone, are also provided.

20 Claims, 18 Drawing Sheets

(56) References Cited

U.S. PATENT DOCUMENTS

| | | |
|---|---|---|
| 6,639,153 B2 | 10/2003 | Hauge |
| 6,770,084 B1 | 8/2004 | Bain et al. |
| 7,329,272 B2 | 2/2008 | Burkhart et al. |
| 7,588,587 B2 | 9/2009 | Barbieri et al. |
| 7,879,048 B2 | 2/2011 | Bain et al. |
| 7,993,369 B2 | 8/2011 | Dreyfuss |
| 8,118,835 B2 | 2/2012 | Weisel et al. |
| 8,430,909 B2 | 4/2013 | Dreyfuss |
| 8,579,940 B2 | 11/2013 | Dreyfuss et al. |
| 8,925,158 B2 | 1/2015 | Fried |
| 8,936,620 B2 * | 1/2015 | Kaiser ................ A61B 17/0401 606/232 |
| 9,131,937 B2 | 9/2015 | Chan et al. |
| 9,179,907 B2 | 11/2015 | ElAttrache et al. |
| 9,314,088 B2 | 4/2016 | Lesch |
| 9,427,266 B2 | 8/2016 | Kmiec, Jr. |
| 9,706,986 B2 | 7/2017 | ElAttrache et al. |
| 9,775,599 B2 | 10/2017 | ElAttrache et al. |
| 10,052,091 B2 | 8/2018 | Dreyfuss et al. |
| 10,582,920 B2 | 3/2020 | Lunn et al. |
| 10,709,436 B2 | 7/2020 | Burkhart et al. |
| 10,716,556 B2 | 7/2020 | ElAttrache et al. |
| 2006/0276841 A1 | 12/2006 | Barbieri et al. |
| 2007/0225719 A1 * | 9/2007 | Stone ................ A61B 17/0642 606/232 |
| 2009/0005794 A1 | 1/2009 | Lowry |
| 2009/0306711 A1 | 12/2009 | Stone et al. |
| 2010/0016892 A1 * | 1/2010 | Kaiser ................ A61B 17/0401 606/232 |
| 2011/0071551 A1 | 3/2011 | Singhatat et al. |
| 2011/0264140 A1 * | 10/2011 | Lizardi ............. A61B 17/0401 606/232 |
| 2013/0158599 A1 * | 6/2013 | Hester ................ A61B 17/0401 606/232 |
| 2015/0201923 A1 | 7/2015 | Fan et al. |
| 2015/0216662 A1 | 8/2015 | Medema et al. |
| 2018/0235598 A1 | 8/2018 | Burkhart et al. |

OTHER PUBLICATIONS

European Search Report for Application No. 22157542.6 issued Jul. 27, 2022 (13 pages).

* cited by examiner

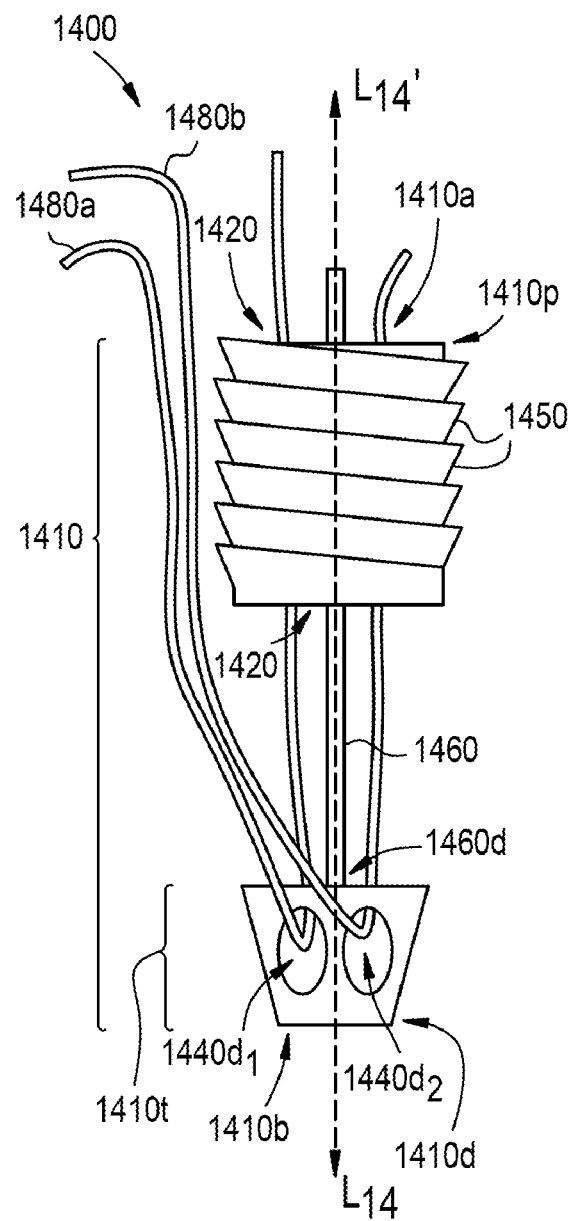
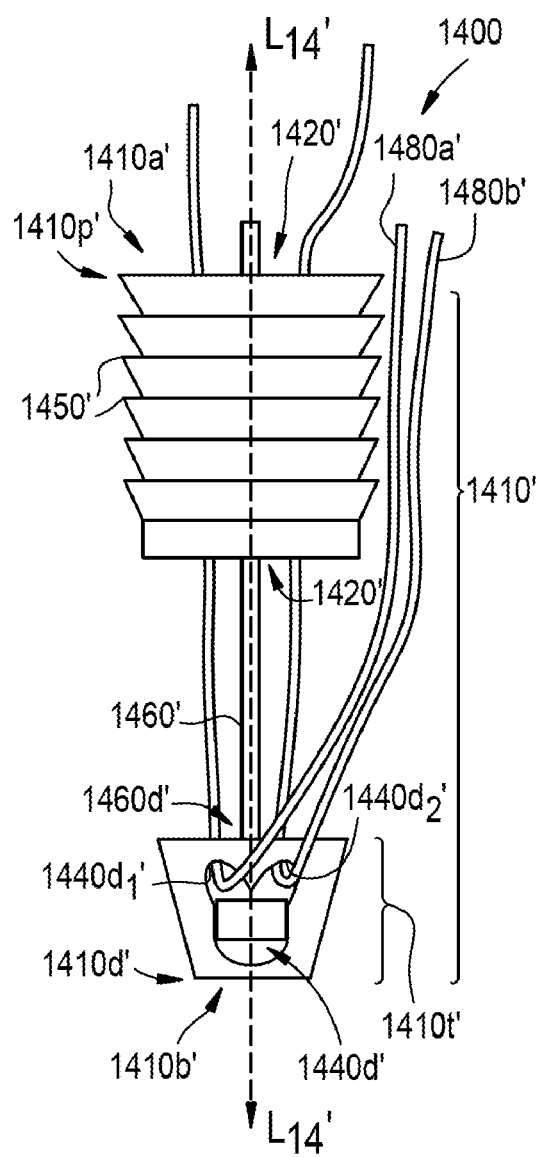
FIG.19A
FIG. 19B

FIG. 22A
FIG. 22B
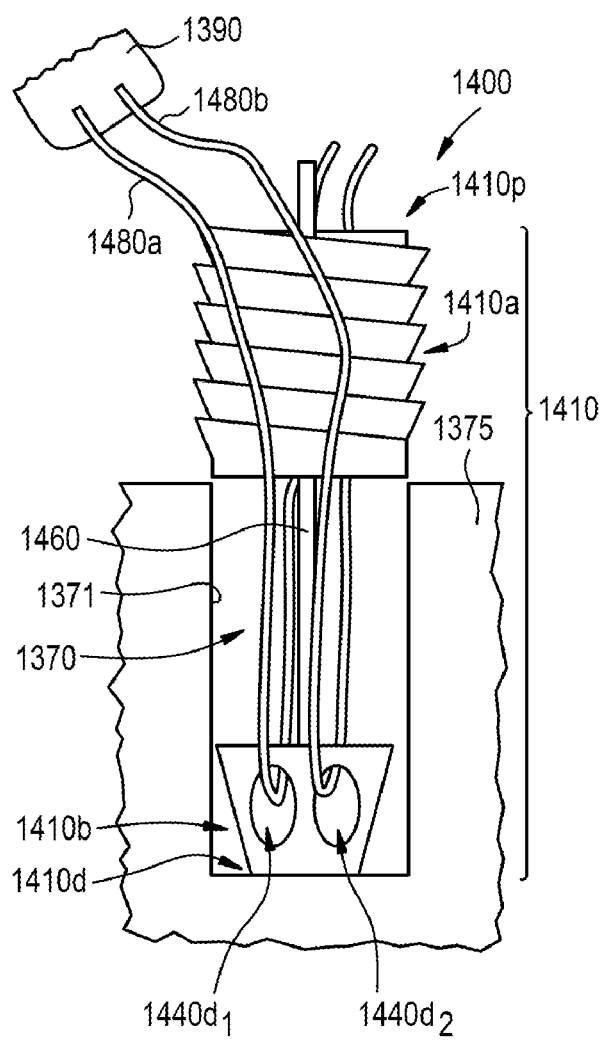
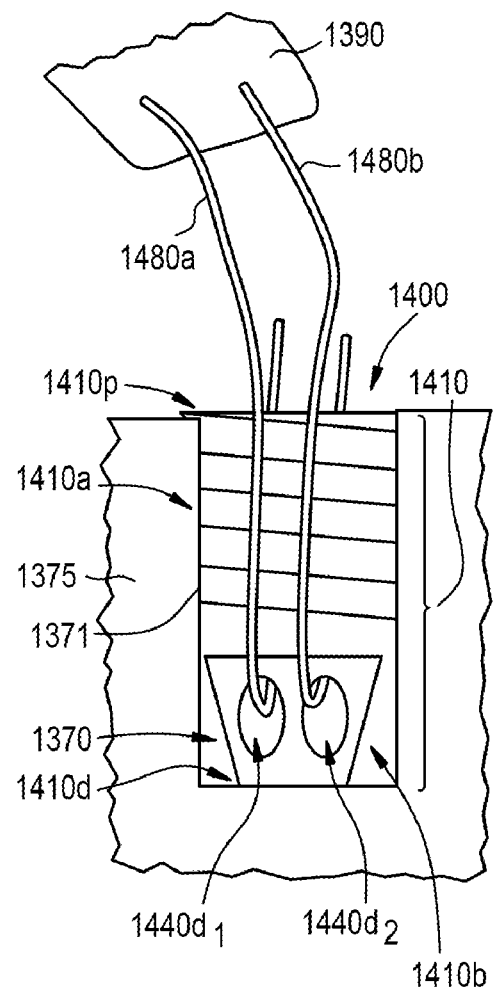

KNOTLESS INSTABILITY DEVICES AND METHODS FOR SOFT TISSUE REPAIR

FIELD

The present disclosure relates to devices and methods for affixing soft tissue to bone, and more particularly to knotless suture anchors and methods for use in performing soft tissue repairs.

BACKGROUND

Many surgical procedures involve placing an implant into bone. For example, in instances where soft tissue injury result in partial or complete detachment of soft tissue (e.g., ligament and/or tendon) from associated bones, reattachment of the detached soft tissue to bone may be necessary. In such instances, surgical procedures involving bone implants can be used to reattach soft tissue to bone. A common type of bone implant used for soft tissue repair is a suture anchor in combination with a suture. For example, soft tissue can be coupled to a suture, and the suture can be tied to or otherwise secured by a suture anchor that is disposed in a bone to which the soft tissue is being attached. The suture anchor can be implanted into the bone by being driven directly into the bone or the suture anchor can be secured within a pre-formed or pre-existing hole in the bone.

Knotless suture anchors are a type of suture anchors configured such that a surgeon does not need to tie any knots during the procedure. For example, some knotless suture anchors secure suture limbs (strands) to the bone by trapping the suture limbs between an inner surface of the hole and an outer surface of the suture anchor. The knotless suture anchor can be a single component suture anchor. Alternatively, the knotless suture anchor can be a multi-component system that includes, for example, an insertion rod, a suture-engaging member, and a suture anchor member such that the insertion rod can first guide a suture-engaging member into the hole in the bone to bring a portion of suture limbs to the hole and, subsequently, secure a portion of the inserted suture limbs to the bone by inserting a suture anchor member into the hole.

One challenge posed by currently available knotless suture anchors is the inability to properly manipulate suture limbs during a soft tissue repair surgery. Proper manipulation of suture limbs during soft tissue repair surgeries is important for many reasons. For example, suture limbs may need to be manipulated to ensure proper tensioning of the suture limbs that are attached to the soft tissue to properly position the soft tissue with respect to the bone prior to complete insertion of the suture anchor into the bone. Improper manipulation of the suture limbs can result in under- or over-tensioning of the suture limbs prior to anchor implantation. Additionally, suture limbs may need to be manipulated to ensure that portions of the suture limbs that are being trapped between the bone hole surface and the suture anchor surface do not cross because frictional force that is holding the suture limbs to the bone may be significantly reduced when the suture limbs cross, resulting in insufficient retention of the suture limbs. Such insufficient retention of the suture limbs can cause sliding out (or otherwise deviating) of the suture limbs from the intended secured position.

It is therefore desirable to provide devices and methods for use in soft tissue repair that allows for improved manipulation of the suture limbs to ensure proper tensioning of suture limbs and prevention of the portions of suture limbs being secured between the bone and the suture anchor from crossing.

SUMMARY

Devices and methods are generally provided for securing soft tissue to bone. The devices and methods can also be adapted for use in securing one or more objects, such as bone fragments or tissue, and for drawing two or more tissues together so they can be secured in a desired location, among other surgical procedures.

In one exemplary embodiment, a suture implantation assembly includes an insertion rod, a distal tip member removably coupled to the insertion rod, and a proximal main member. The distal tip member has a suture engagement feature that is configured to have a plurality of suture limbs slidably coupled to it. The proximal main member has an elongated cylindrical body with one or more bone-engaging features disposed on its outer surface. The proximal main member also includes a longitudinal lumen that extends from a proximal end to a distal end. The proximal main member is slidably disposed on the insertion rod by having the insertion rod removably disposed through the longitudinal lumen. The proximal main member is proximal of the distal tip member, and the proximal main member is configured to have a plurality of suture limbs that are slidably coupled to the distal tip member passed through at least a portion of the elongated cylindrical body in a proximal direction from a first location on the elongated cylindrical body to a second location on the elongated cylindrical body. The first location is closer than the second location is to the distal end of the elongated cylindrical body. One of the distal tip member and the proximal main member includes a first suture limb holding surface formed on a first side of a central longitudinal axis that extends centrally through the longitudinal lumen from a profile view and a second suture limb holding surface formed in it on a second side of the central longitudinal axis from the profile view, the second side being opposed to the first side with respect to the central longitudinal axis. A portion of the first suture limb holding surface that is closest to a proximal end of the distal tip member is located separate from a portion of the second suture limb holding surface that is closest to a proximal end of the distal tip member such that a first limb of the plurality of suture limbs that are slidably coupled to the distal tip member can be disposed against the portion of the first suture limb holding surface that is closest to the proximal end of the distal tip member and a second limb of the plurality of suture limbs that are slidably coupled to the distal tip member can be disposed against the portion of the second suture limb holding surface that is closest to the proximal end of the distal tip member. As a result, first and second suture limbs are maintained a distance apart from each other.

The first suture limb holding surface can include a first bore and second suture limb holding surface can include a second bore. The first and second bores can be on the first and second sides of the central longitudinal axis. Alternatively, the first suture limb holding surface can be a part of a first lobe and the second suture limb holding surface can be part of a second lobe. The first and second lobes can be portions of a single bore. Further, proximal-most portions of the first and second lobes can be on the first and second sides of the central longitudinal axis.

In some embodiments, the first and second suture limb holding surfaces can be located on the distal tip member, while in some embodiments the first and second suture limb holding surfaces can be located on the proximal main member. In the latter instances, the first and second suture limb holding surfaces can be part of at least one opening formed in the proximal main member. In some such embodiments, a distal-most end of the opening can be disposed at the distal-most end of the proximal main member, which can create a location at which the first and second suture limbs can enter the at least one opening to slidably couple to the first and second suture limb holding surfaces.

In some other embodiments, the first and second suture limb holding surfaces are part of at least one opening formed in the proximal main member such that a distal-most end of the opening is disposed at the distal-most end of the proximal main member. As a result, a location is created at which the first and second suture limbs can enter the at least one opening to slidably couple to the first and second suture limb holding surfaces.

One or more projections can be disposed radially outward from an outer surface of a distal portion of the proximal main member. The projection(s) can be configured such that when a relatively planar surface disposed proximate to an entry location of a bore is engaged with a distal end of the projection(s), at least a portion of at least one of the first and second suture limb holding surfaces is disposed proximal of the relatively planar surface. As a result, at least one of first or second limbs of the plurality of suture limbs that is slidably coupled to the respective first and second holding surfaces can remain slidable relative to the respective first and second holding surface. In some such embodiments, the distal end of at least one projection of the one or more projections can be tapered radially outward as the projection extends towards the proximal end of the proximal main member.

A flared portion can be disposed at the proximal end of the proximal main member. A combination of the flared portion and any portion of the one or more bone-engaging surfaces formed on the flared portion can have a diameter that is greater than a diameter formed by a combination of the proximal main member distal of the flared portion and the one or more bone-engaging surfaces disposed on the outer surface of the proximal main member.

One exemplary embodiment of a surgical procedure of affixing tissue to a bone includes coupling a suture to tissue such that two suture limbs extend from the tissue and coupling each of the two suture limbs to one or more suture engagement features of a distal tip member of a suture anchor such that the two suture limbs are slidably disposed with respect to the one or more suture engagement features. The method further includes inserting the distal tip member into a bore formed in bone and passing the two suture limbs from the one or more suture engagement features of the distal tip member into and through at least a portion of a proximal main member of the suture anchor. The two suture limbs are positioned such that a first limb of the two suture limbs is engaged with a first surface defining a portion of at least one opening formed in one of the distal tip member and the proximal main member located on a first side of a central longitudinal axis that extends centrally through the suture anchor from a profile view and a second limb of the two suture limbs is engaged with a second surface defining a portion of at least one opening formed in one of the distal tip member and the proximal main member located on a second side of the central longitudinal axis that is opposed to the first side from the profile view such that the first and second limbs are maintained a distance apart from each other on the opposite sides of the central longitudinal axis. The method still further includes applying tension to at least one of the two suture limbs to draw the tissue towards the bone and advancing the proximal main member distally towards the distal tip member to lock a location of the two suture limbs, and thus the tissue coupled to the bone, at a location relative to the bone.

In some embodiments, the at least one opening can be formed in the distal tip member and the one or more suture engagement features can include the at least one opening. In some such embodiments, coupling each of the two suture limbs to one or more suture engagement features of the distal tip member can also include engaging the first limb with the first surface of the at least one opening and engaging the second limb with the second surface of the at least one opening. In some alternative embodiments, the at least one opening is formed in the proximal main member. In some such embodiments, the action of coupling each of the two suture limbs to one or more suture engagement features of the distal tip member can occur prior to the action of passing the two suture limbs from the one or more suture engagement features of the distal tip member into and through at least a portion of the proximal main member of the suture anchor.

The action of inserting the distal tip member into a bore formed in bone can include advancing an insertion rod having the distal tip member coupled to it towards the bore formed in bone. In some such embodiments the proximal main member can be slidably disposed on the insertion rod. Advancing the proximal main member distally towards the distal tip member to lock a location of the two suture limbs can include inserting the proximal main member into the bone hole such that surface engagement features formed on an outer surface of the elongate body engage surfaces of the bone that define the bore.

In some embodiments, the surgical procedure can also include moving the proximal main member towards the bore formed in the bone until one or more protrusions disposed on the proximal main member engage the bone proximate to the bore such that the proximal main member cannot advance further towards the bore without application of an additional amount of force to the proximal main member. The engagement of the one or more protrusions with the bone can provide a gap between the proximal main member and a proximal edge of the bore, thereby accommodating movement of the suture limbs with respect to the first and second surfaces. Advancing the proximal main member distally towards the distal tip member to lock a location of the two suture limbs can result in elimination of the gap.

One exemplary embodiment of a suture anchor includes an elongate anchor body, one or more bone-engaging surfaces, and at least one side opening formed in the outer surface. More particularly, the elongate anchor body includes a proximal end, a distal end, and a longitudinal lumen extending through a length of the elongate anchor body from the distal end to the proximal end. A distal tip portion associated with the distal end of the suture anchor is tapered such that a diameter defined by an outer surface of the elongate anchor body at the distal end is less than a diameter defined by the outer surface of the elongate anchor body at a proximal end of the distal tip portion. The one or more bone-engaging surfaces are disposed on the outer surface of the elongate anchor body and configured to engage bone. The at least one side opening is formed in the outer surface of the elongate anchor body and is in direct communication with the longitudinal lumen such that suture limbs can be passed through the side opening and into the longitudinal lumen. A proximal end of the at least one side opening has a shape such that at least two separate suture guiding paths are formed. The at least two separate suture guiding paths include a first suture guiding path disposed on a first side of a central longitudinal axis extending through the at least one side opening from a profile view, and a second suture guiding path disposed on a second side of the central longitudinal axis from the profile view, the second side being opposed to the first side.

In some embodiments, a shape of the at least one side opening can include a scalloped portion. In some such embodiments the at least one side opening can include a distal portion that includes a channel and a proximal portion that includes the scalloped portion. The scalloped portion can include the first and second guiding paths.

The anchor can also include one or more projections disposed radially outward from the outward surface of a distal portion of the suture anchor. At least one of the projections can be configured such that when a relatively planar surface disposed proximate to an entry location of a bore is engaged with a distal end of the at least one projection, at least a portion of at least one of the first and second suture guiding paths is disposed proximal of the relatively planar surface so that a suture limb passed through the side opening and into the longitudinal lumen is slidably coupled to the respective first and second suture guiding paths and can be slid relative them.

In some embodiments, the distal end of at least one projection can be tapered radially outward as the projection extends towards the proximal end of the suture anchor. The projection can further include a proximal end that is not tapered radially outward as the projection extends towards the proximal end of the suture anchor.

A flared portion can be disposed at the proximal end of the elongate anchor body. A combination of the flared portion and any portion of the one or more bone-engaging surfaces formed on the flared portion can have a diameter that is greater than a diameter formed by a combination of the elongate anchor body distal of the flared portion and the one or more bone-engaging surfaces disposed on the outer surface of the elongate anchor body.

BRIEF DESCRIPTION OF DRAWINGS

FIG. 19A is a schematic side view of yet another exemplary embodiment of a suture anchor;

FIG. 19B is a schematic side view of another exemplary embodiment of a suture anchor;

FIG. 22A-22B are schematic side views of the suture anchor of FIG. 19A in use.

DETAILED DESCRIPTION

Figure 1A:
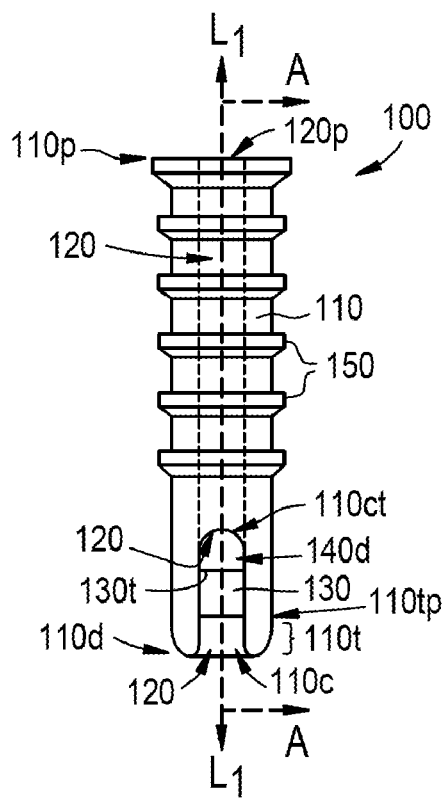
FIG. 1A is a front view of one exemplary embodiment of a suture anchor.
Figure 1B:
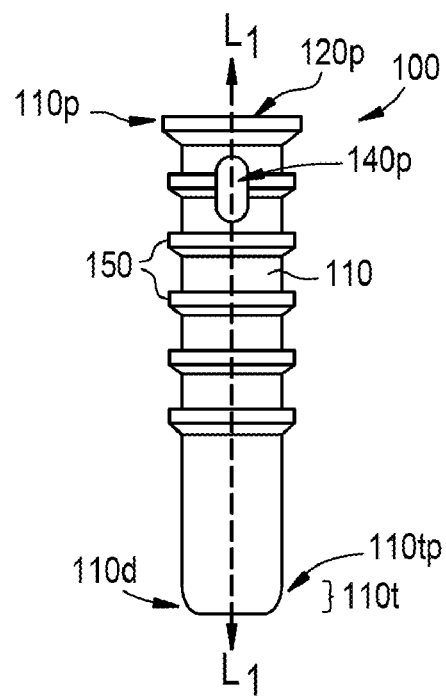
FIG. 1B is a back view of the suture anchor of FIG. 1A.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment can be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Sizes and shapes of the devices, and the components thereof, can depend at least on the anatomy of the subject in which the devices will be used, the size and shape of components with which the devices will be used, and the methods and procedures in which the devices will be used. The figures provided herein are not necessarily to scale, and at least some are schematic illustrations that a person skilled in the art would recognize how to size, dimension, and use the illustrated embodiments in the context of a surgical procedure in view of the teachings herein and their knowledge in the art.

Devices and methods are generally provided for securing soft tissue to a bone. In general, the devices and methods allow securing soft tissue to the bone using a suture coupled to a suture anchor without tying a knot or otherwise tie the suture to secure the soft tissue in place relative to the bone. A suture anchor can, as illustrated in some embodiments described herein, include two or more parts, sometimes described as a suture implantation assembly that comprises multiple components.

The devices include features that are configured to improve suture manipulation during implantation of suture anchor, which results in improved soft tissue affixture to tissue. Specifically, the devices have features that allow tensioning of suture strands prior to fully inserting the suture anchor into an anchor accepting bone hole to lock suture limbs and features that help a user to prevent unintentional and/or accidental "crossing" of the suture limbs at portions of the suture limbs that are fixed and/or locked between an inner surface of the bone hole and an outer surface of the suture anchor. While the devices and methods disclosed herein are for anchoring soft tissue to the bone, the methods and devices can be used in other medical procedures for anchoring various objects to one another.

Figure 1C:
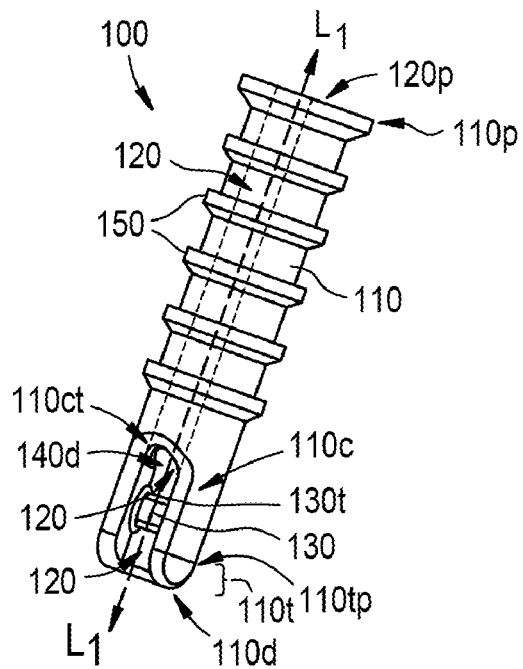
FIG. 1C is an isometric view of the suture anchor of FIG. 1A.
Figure 1D:
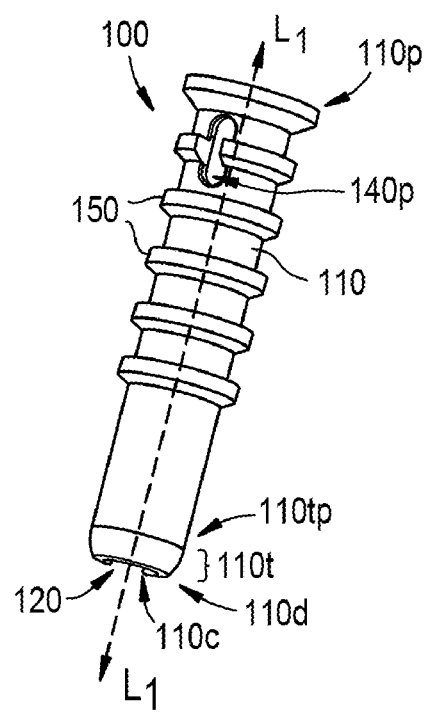
FIG. 1D is another isometric view of the suture anchor of FIG. 1A.
Figure 2A:
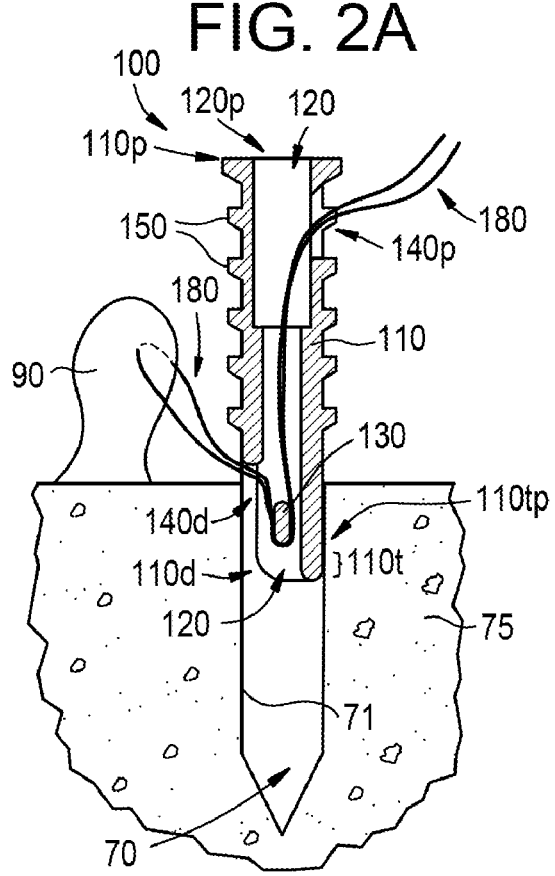
FIGS. 2A-2B are cross-sectional views of the suture anchor of FIG. 1A taken along line A-A as the anchor is disposed in a bore in a bone.

In one exemplary embodiment, as shown in FIGS. 1A-1D, a suture anchor 100 can include a generally cylindrical elongate body 110 extending from a proximal end 110p to a distal end 110d along a longitudinal axis $L_1$ thereof. The distal end 110d can be more generally part of a distal portion of the elongate body 110, with the distal portion including a tapered distal portion 110t and a cutout portion 110c. A longitudinal lumen 120 can extend from the distal portion of the elongate body 110 to the proximal end 110p. As shown, the lumen 120 can be centrally disposed such that the longitudinal axis $L_1$ extends therethrough and the lumen 120 is coaxial to the cylindrical elongate body 110 of the suture anchor 100, although other configurations are possible. As shown in FIG. 2A, a proximal portion of the lumen 120 can have a greater diameter than a distal portion, which can help accommodate a distal tip of an inserter or other insertion device for the suture anchor 100. As discussed in greater detail below, the cutout portion 110c helps define aspects of a distal side opening 140d and provides access to a suture-engaging feature 130. In the illustrated embodiment the cutout portion 110c has an elongate, curved profile, as best illustrated in FIGS. 1A and 1C, although other configurations are possible.

The outer surface of the elongate body 110 can include one or more bone-engaging features 150. In the illustrated embodiment the bone-engaging features 150 include a plurality of radially extending protrusions or ribs formed on the outer surface of the suture anchor 100, but a person skilled in the art will recognize other suitable bone-engaging features that can be used in the context of helping the elongate body 110 be securely situated within bone. One such non-limiting example is provided for in FIG. 19A, in which a bone-engaging feature includes a single cork-screw shaped thread 1450. A person skilled in the art will appreciate that changes can be made to the geometry of the bone-engaging features 150 to increase a compression force exerted between the bone-engaging features 150 of the bone anchor 100 and an inner surface or wall 71 of the bone hole 70, such as the bone-engaging feature 150 having dimensions that can be larger than a diameter of the bone hole 70 at the widest parts of the bone-engaging feature 150. Likewise, a person skilled in the art will appreciate that changes can be made to the geometry of the bone-engaging features 150 to help prevent unintended dislodging of the suture anchor 100 (i.e., the suture anchor 100 moving proximally after being inserted into the bone hole 70), thus ensuring that the suture anchor 100 remains in the bone hole 70 to lock the suture limbs 180 relative to the bone 75.

The distal portion of the elongate body 110 can also include a suture-engaging feature 130. The suture-engaging feature 130 can be described as disposed within the lumen 120 such that the lumen 120 extends from the distal end 110d to the proximal end 110p and the suture-engaging feature 130 is disposed within a length of the lumen 120. The lumen 120 can be coaxial with the elongate body 110. Alternatively, the lumen 120 can be described as terminating at a location of a distal side opening 140d and then a separate lumen, substantially aligned with the lumen 120, can be described as existing below the suture-engaging feature. Both interpretations can be appropriate, although for ease of reference the present illustration shows the lumen 120 as extending through to the distal end 110d. Further, both interpretations can result in openings being formed on the surfaces of the distal and proximal ends 110d, 110p of the cylindrical elongate body 110.

Figure 2B:
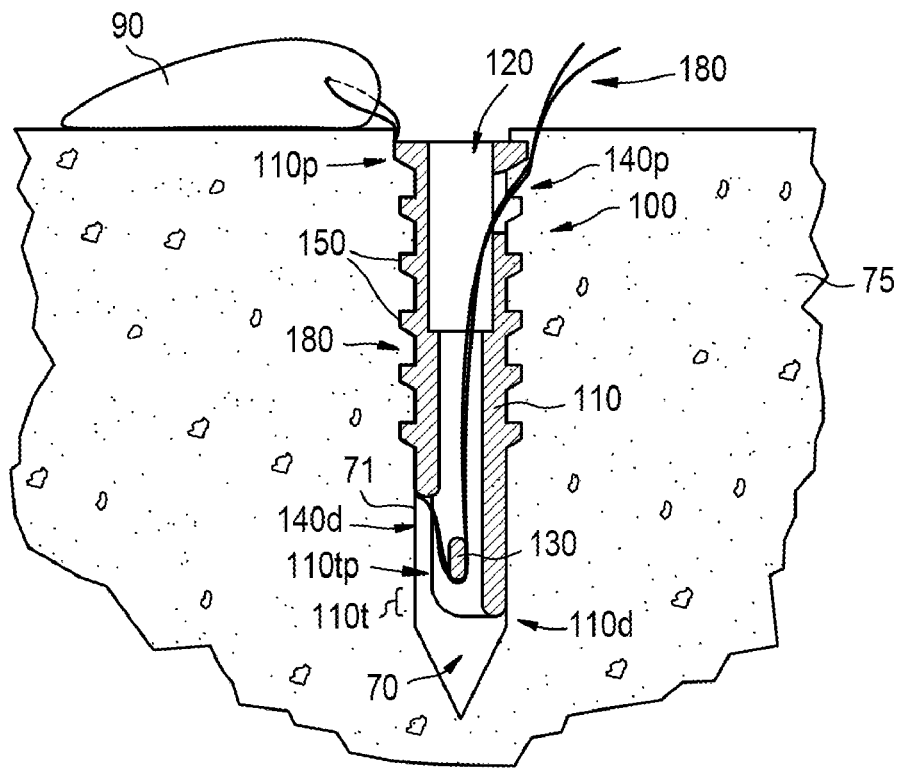

The suture-engaging feature 130 can be a structure to which suture limbs, such as suture limbs 180 in FIGS. 2A-2B, can be slidably coupled. In some embodiments, as shown in FIG. 1C, the suture-engaging feature 130 can comprise a bridge member (e.g., saddle or pulley-like member). In the illustrated, non-limiting embodiment of the bridge member of FIG. 1C, the suture-engaging feature includes a rod-shaped member extending substantially transverse to the central longitudinal axis $L_1$ of the suture anchor 100 from one side of the internal surface of the longitudinal lumen 120 of the suture anchor 100 to an opposite side. The suture-engaging feature 130 can improve suture manipulation (e.g., tensioning of suture limbs to position soft tissue associated with the suture limbs to bone, as described in greater details with respect to FIGS. 2A-2B) during a surgical procedure. More particularly, in the illustrated embodiment, the bridge member that forms the suture-engaging feature 130 provides "pulley-like" features that allow suture to easily slide around it during use. One skilled in the art would appreciate that a suture-engaging feature 130 can comprise other shapes and structural features, including but not limited to such suture-engaging features described herein with respect to at least FIGS. 4, 7A, and 14A. Access to the suture-engaging feature 130 can be provided by the cutout portion 110c, which in turn can result in access being provided by the distal side opening 140d, as well as the longitudinal lumen 120.

At least one side opening 140p, 140d can be formed on an outer surface of the elongate anchor body 110. The illustrated embodiment includes two side openings, with the distal side opening 140d being disposed at a location with respect to the body 110 that is above and proximate to the suture-engaging feature 130 and a proximal side opening 140p being disposed at a location with respect to the body 110 that is below and proximate to the proximal end 110p. More particularly, the distal side opening 140d is defined by a top surface 130t of the suture-engaging feature 130 and a proximal-most surface 110ct of the cutout portion 110c. In a profile view, such as illustrate by FIG. 1A, the resulting distal side opening 140d can have a door-like shape. In the embodiment, as more clearly illustrated in FIGS. 2A and 2B, the proximal-most surface 110ct can serve as a suture limb holding surface because suture limbs may engage the surface in use. Alternatively, the proximal-most surface 110ct may not necessarily hold the surface, for example if the suture-engaging feature 130 is positioned in a manner that causes a suture limb passing thereby to not actually engage the proximal-most surface 110ct.

The proximal side opening 140p is formed through the anchor body 110. In the illustrated embodiment, it has an elongate, elliptical shape. More generally, the one or more side openings 140p, 140d can be in direct communication with the longitudinal lumen 120 such that a suture can be passed through one or more of the one or more side openings 140p, 140d and the longitudinal lumen 120 in conjunction with the suture being disposed onto, around, or otherwise associated with the suture-engaging feature 130. Still further, a person skilled in the art will appreciate other sizes, shapes, and configurations for the openings 140p, 140d, or other side openings provided for in an anchor, can be used without departing from the spirit of the present disclosure. Other appropriate terms for the side openings 140p, 140d can include slots, eyelets, or keyways, among other descriptions, shapes, sizes, and configurations.

As shown more clearly in FIG. 2A-2B, such direct communication between the distal side opening 140d, the longitudinal lumen 120, and the proximal side opening 140p can allow suture limbs 180, as shown two limbs, to enter the suture anchor 100 through the distal side opening 140d, into and through the longitudinal lumen 120, and exit the suture anchor through the proximal side opening 140p, prior to reaching the proximal end 110p of the elongate body 110. This configuration may help provide additional compression for a short length due to the suture limbs 180 being able to be trapped by the proximal portion of the anchor 100, as shown the outer surface of the body 110 between the top of the proximal side opening 140p and a terminal portion of the proximal end 110p, illustrated in FIG. 2B.

As shown in FIGS. 2A-2B, the suture anchor 100 can be sized and shaped to fit and be fixed into a corresponding bone hole or bore 70 formed in bone 75. The bone hole 70 can be pre-drilled or a pre-existing bore in a bone 75 that is designed to accept the suture anchor 100. As described and illustrated herein, the bone hole 70 can provide a surface 71 such that suture limbs 180 can be disposed between the surface 71 of the bone hole 70 (e.g., inner surface of the bone hole 70) and an outer surface of the suture anchor 100, which as shown can include the bone-engaging features 150.

While in some embodiments the suture anchor 100 can include a distal side opening 140d and a proximal side opening 140p, in other embodiments only the distal side opening 140d may exist. In some instances, suture can be passed through an opening 120p defined by the longitudinal lumen 120 at the proximal end 110p of the body 110. One example is illustrated with respect to FIGS. 9A-10, in which a suture anchor 500 includes only a distal side opening 540d and not a separate proximal side opening and suture 580 is passed through an opening 520p of a longitudinal lumen 520, described in further detail below. Additional side openings can also be formed in the body 110 as desired, providing alternative ways or paths by which suture can be passed into and out of the anchor 100 and into and out of communication with the outer surface of the anchor and/or the bone surface 71 defined by the bone 75 forming the bone hole 70. As a result, many different configurations in which various portions of suture limbs can be trapped between the body 110 and the bone surface 71 for various lengths within the bone hole 70.

The bone-engaging features 150 can also serve as suture-engaging features, in addition to or lieu of the suture-engaging feature 130. As shown in FIG. 2B, the bone-engaging features 150 can improve securing, or otherwise locking or affixing, the suture limbs 180 relative to the bone 75 by enhancing the retention force that is securing the limbs 180 in place by the anchor 100. For example, an increase in lengths of the portions of suture limbs 180 that are in contact with the suture anchor 100 and/or the surface 71 of the bone hole 70 can increase the total friction that exists between the suture anchor 100 and the suture limbs 180 and/or the suture limbs 180 and the bone hole surface 71. The securement of the suture limbs 180 between the anchor 100 and the surface 71 can be further enhanced by the shape and size of the bone-engaging features 150, just as the shape and size of the bone-engaging features 150 can further enhance the securement of the anchor 100 relative to the bone 75.

In some embodiment, a distal tip portion 110t of the suture anchor 100 can be tapered (e.g., distally towards the central axis $L_1$) such that a diameter defined by an outer surface of the distal end 110d of the body 110 is less than a diameter defined by an outer surface of the body 110 at a proximal end 110tp of the distal tip portion 110t and/or the diameter of the bone hole 70 into which the anchor 100 is inserted. Such tapered distal tip portion 110t of the suture anchor 100 can facilitate insertion of the suture anchor 100 into the bone hole 70 by making it easier for a user to insert the distal tip portion 110*t* of the suture anchor 110 into bone hole 70 because the distal end 110*d* of the elongate body 110 has a diameter that is smaller than a diameter of the bone hole 70. Further, the illustrated curve, which in alternative embodiments can be a more linear, angled, but straight surface, can help start the anchor 100 into the bone hole 70.

FIGS. 2A and 2B help illustrate one, non-limiting exemplary embodiment of a surgical procedure that can be performed using the suture anchor 100 to secure tissue 90 to bone 75. The suture limbs 180 can be coupled to or otherwise engaged with the tissue 90 intended to be secured to the bone 75. This can be accomplished, for example, by inserting one end of one or both suture limbs 180 through the tissue 90 as shown. In other non-limiting instances, this can include wrapping one or both suture limbs 180 around the tissue 90. After becoming coupled to or otherwise associated with the tissue 90, the suture limbs 180 can extend from the tissue 90 and be manipulated with respect to the anchor 100. In the illustrated embodiment, the suture limbs 180 extend from the tissue 90, passed into the suture anchor 100 by way of the distal side opening 140*d*, and are slidably coupled to or otherwise associated with the suture-engaging feature 130. The suture limbs 180 can slide easily relative to the suture-engaging feature. The limbs 180 can then extend from the suture-engaging feature 130 and proximally through at least a portion of the longitudinal lumen 120. As shown, the limbs 180 extend through the lumen 120 and exit the anchor 100 through the proximal side opening 140*p*. Alternatively, they can be passed through the longitudinal lumen 120 at the terminal portion of the proximal end 110*p* of the body 110 (i.e., a terminal end or proximal terminal end).

Notably, while in the illustrated embodiment both suture limbs 180 follow the same path, in other embodiments, they can take different paths, such as one passes through the longitudinal lumen 120 at the terminal portion of the proximal end 110*p* of the body 110 while the other passes through the proximal side opening 140*p*. By way of further non-limiting embodiment, one limb can pass through the distal side opening 140*d*, around the suture-engaging feature 130, and extend proximally through at least a portion of the longitudinal lumen 120 while another limb can be disposed around the distal end 110*d* of the body 110 (through the distal side opening 140*d* or staying outside of it), and can be passed proximally upward around an opposed outer surface of the body 110 (if it passed through the distal side opening 140*d*, then it could exit the longitudinal lumen 120 at a terminal portion of the distal end 110*d* of the body 110). In at least some instances, more than two suture limbs may be used, and they can take the same or different paths around and/or through the anchor 100 without departing from the spirit of the present disclosure. These configurations, and others, can be set-up typically prior to inserting the anchor 100 into the bone hole 70, or at least prior to inserting the portion of the anchor 100 that includes the distal side opening 140*d* into the bone hole 70 so the opening 140*d* can be easily accessible and the suture limbs 180 can slide easily relative thereto.

Once the suture limbs 180 are coupled to the tissue 90 and the suture anchor 100, the anchor can be inserted into the bone hole 70, or more fully inserted if it is at least partially inserted into the bone hole 70 as shown in FIG. 2A. As the anchor 100 is inserted into the bone hole 70 and the distal side opening 140*d* is disposed within the bone, it will become more difficult to manipulate the suture limbs 180. Insertion will also cause the tissue 90 to become drawn towards the bone hole 70 as the suture limbs 180 get pulled distally into the bone hole 70 and become trapped between the anchor 100 and the surface 71 of bone 75 that defines the bone hole 70. Accordingly, some aspects of desired manipulation of the tissue 90 and/or the suture limbs 180 relative to the anchor 100 should be performed prior to the distal side opening 140*d* becoming disposed within the bone hole 70, prior to it becoming more difficult to slide the suture limbs 180 relative to the anchor 100. For example, prior to insertion, it may be desirable to slide the suture limbs 180 relative to the anchor 100 by applying tension to the suture limbs 180, thereby drawing the tissue 90 towards the anchor 100.

FIG. 2B illustrates the anchor 100 after it has been fully inserted into the bone hole 70. The insertion can be performed using any techniques for disposing an anchor in a bone hole, including but not limited to driven, screwed, pushed, etc. As shown, the suture limbs 180 are affixed relative to the anchor 100 by virtue of being trapped between the anchor 100 and the surface 71 that defines the bone hole 70. As discussed above, engagement of the suture limbs 180 by the anchor 100 and the surface 71 occurs across a substantial length of the outer surface of the body 110 (as shown in FIG. 2B, across the entire exposed length of the outer surface), while because the suture limbs 180 are passed out of the proximal side opening 140*p*, engagement of the suture limbs 180 by the anchor 100 and the surface 71 can occur across a length of the outer surface of the body 110 on the opposed side of the anchor at the proximal end 110*p*. The bone-engaging features 150 help to provide securement between the two. The tissue 90 is drawn towards the bone hole 70, and thus the bone 75, as the anchor 100 is disposed further into the bone hole 70.

Figure 3A:
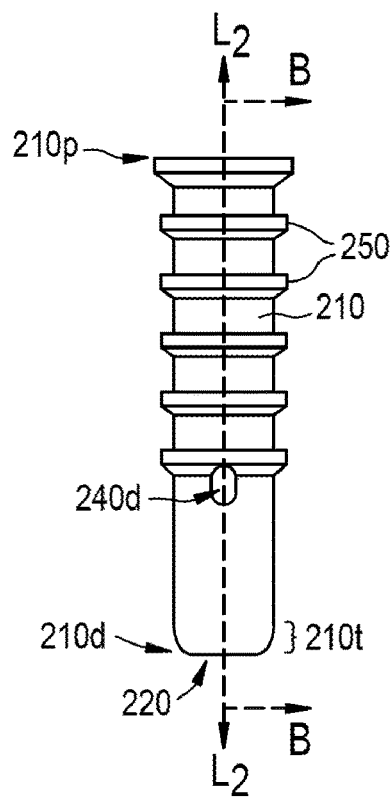
FIG. 3A is a front view of another exemplary embodiment of a suture anchor.
Figure 3B:
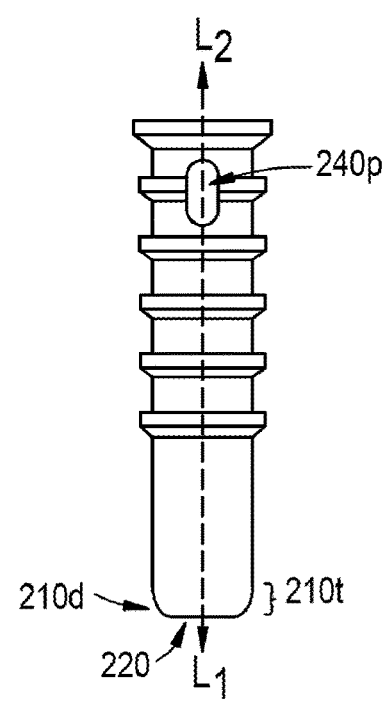
FIG. 3B is a back view of the suture anchor of FIG. 3A.
Figure 3C:
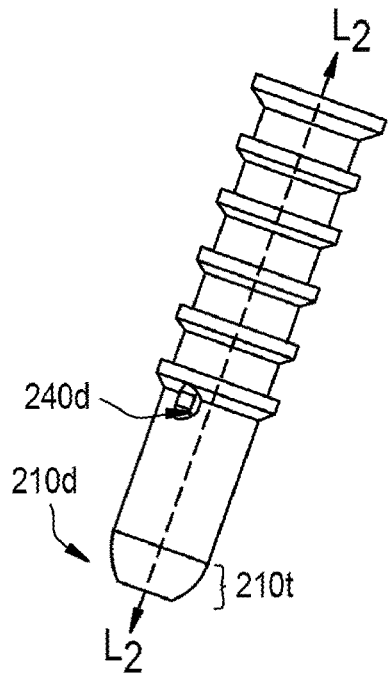
FIG. 3C is an isometric view of the suture anchor of FIG. 3A.
Figure 3D:
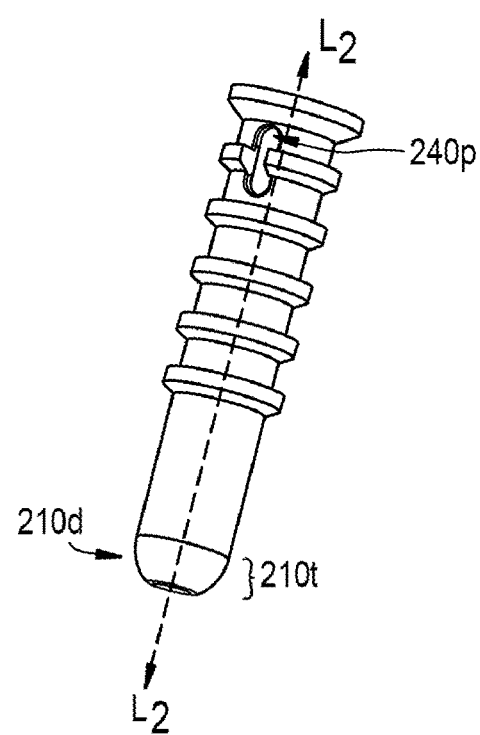
FIG. 3D is another isometric view of the suture anchor of FIG. 3A.
Figure 4:
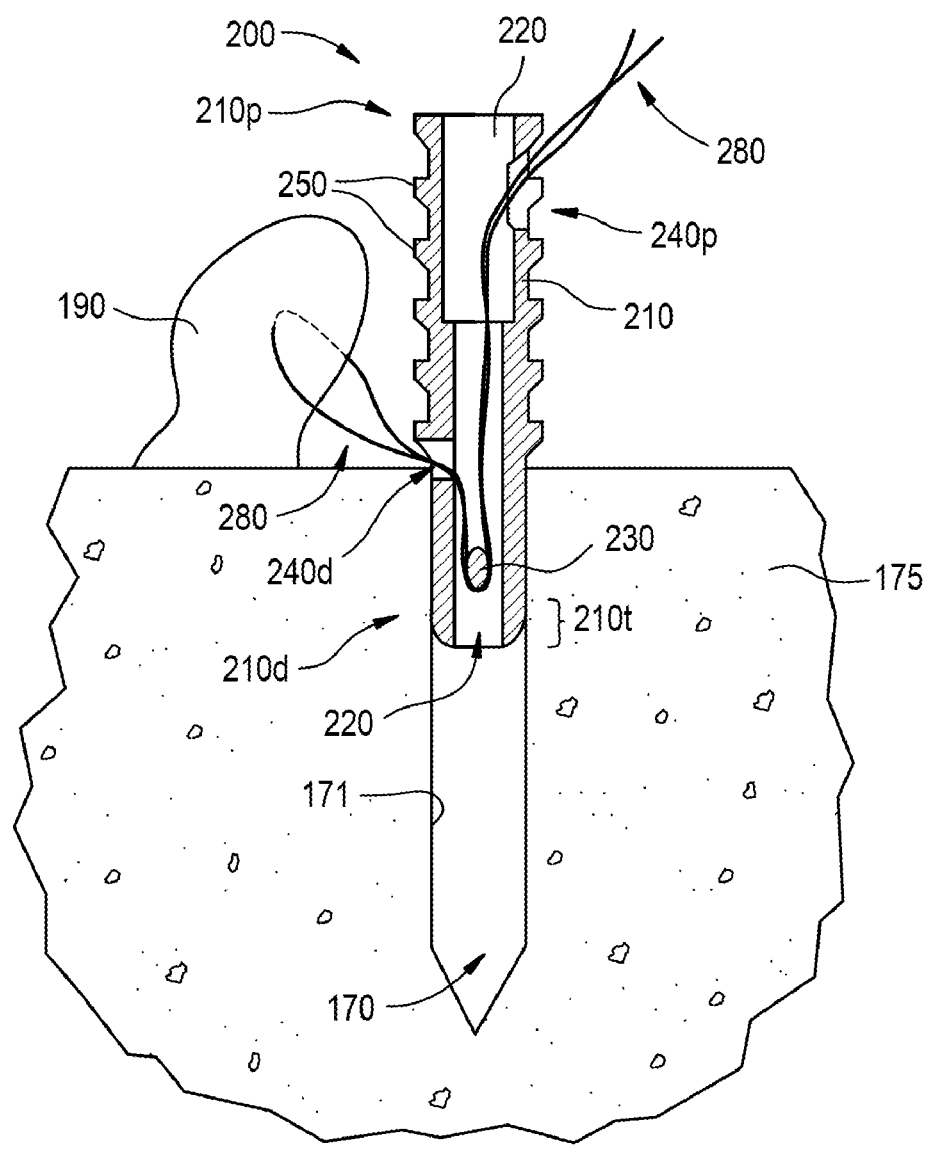
FIG. 4 is a cross-sectional view of the suture anchor of FIG. 3A taken along line B-B prior to fully inserting the anchor in a bore in a bone.

FIGS. 3A-4 illustrate another embodiment of a suture anchor 200. The anchor 200 is similar to the anchor 100 in that it includes an elongate body 210 having proximal and distal ends 210*p*, 210*d* extending along a longitudinal axis $L_2$ thereof, a tapered distal portion 210*t*, a longitudinal lumen 220 extending therethrough, a suture-engaging feature 230 (FIG. 4) disposed in a distal portion of the body 210, within the lumen 220, proximal and distal side openings 240*p*, 240*d*, and bone-engaging features 250. The illustrated embodiment differs from the anchor 100 at least because there is no cutout portion formed in the distal portion of the body 210, the distal side opening 240*d* has a more circular shape as compared to the proximal side opening 240*p*, and the location of the distal side opening 240 vis-à-vis the location of the suture-engaging feature 230 is different. In this last regard, as more clearly illustrated in FIG. 4, suture limbs 280 can pass through the distal side opening 240*d*, extend distally towards and then around the suture-engaging feature 230, before then extending proximally up through the longitudinal lumen 220 and then out of the proximal side opening 240*p*. The shape of the distal side opening 240*d* and the lack of a cutout portion results in, at least in the present embodiment, a distance traveled by the suture limbs 280 from the distal-side opening 240*d* to the suture-engaging feature 230 to be greater than a similar distance traveled by the suture limbs 180 from the distal-side opening 140*d* to the suture-engaging feature 130 of the anchor 100. Otherwise, the configuration and operation of the anchor 200 is similar to that of the anchor 100 unless noted or otherwise understood to operate differently by a person skilled in the art in view of the present disclosures and figures. While in the illustrated embodiment in FIG. 4 the anchor 200 would not engage the suture limbs 280 across an entire length, it will engage the suture limbs 280 across the entire length above the distal side opening 240d, which qualifies as a substantial length of the anchor 200. One benefit of the suture anchor 200 is that because there is more material located at the distal end 210d of the body 210 as compared to the anchor 100, the distal end 210d can provide extra strength and resiliency, which can be beneficial, for example, if the anchor 200 is inserted into a bone hole off-axis. This configuration can make it such that the distal end 210d is less likely to break.

Figure 5A:
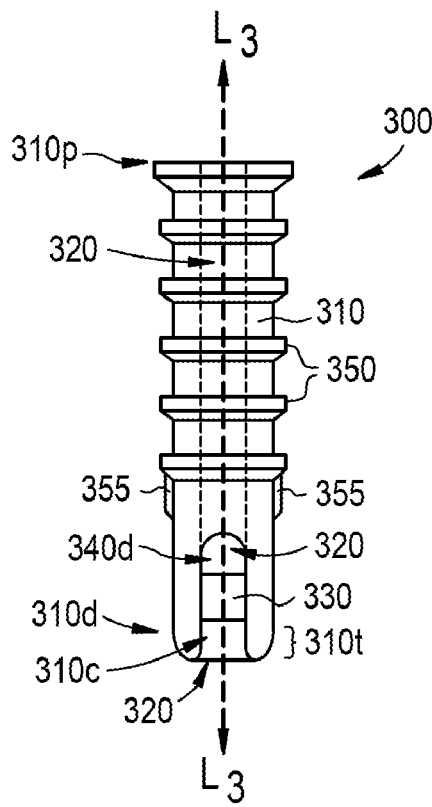
FIG. 5A is a front view of yet another exemplary embodiment of a suture anchor.
Figure 5B:
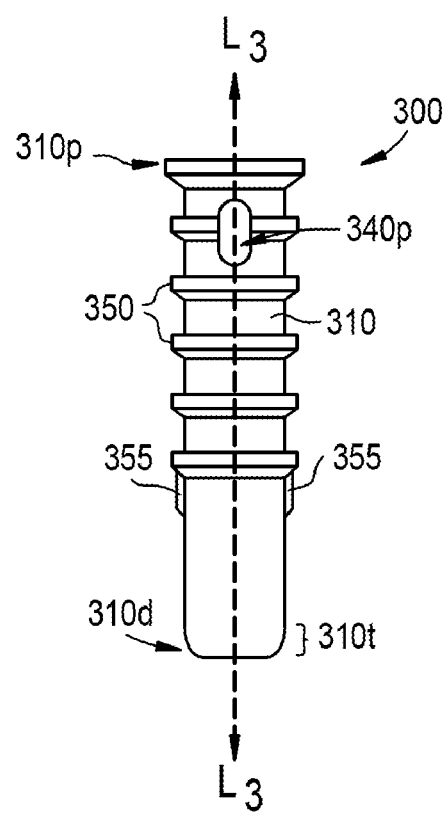
FIG. 5B is a back view of the suture anchor of FIG. 5A.
Figure 5C:
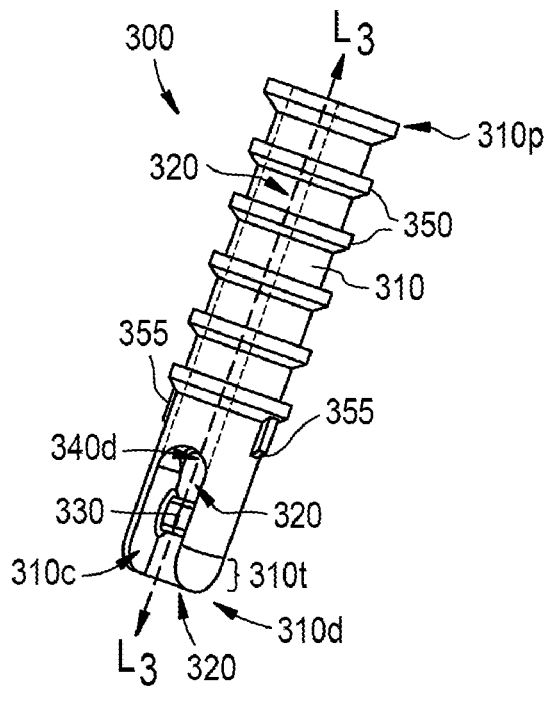
FIG. 5C is an isometric view of the suture anchor of FIG. 5A.
Figure 5D:
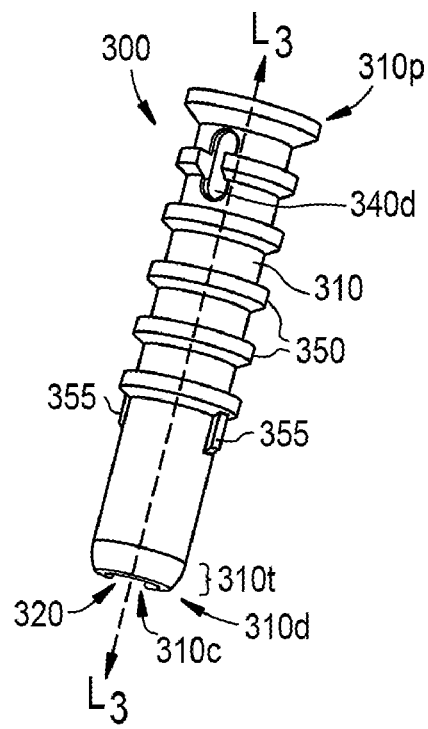
FIG. 5D is another isometric view of the suture anchor of FIG. 5A.
Figure 6:
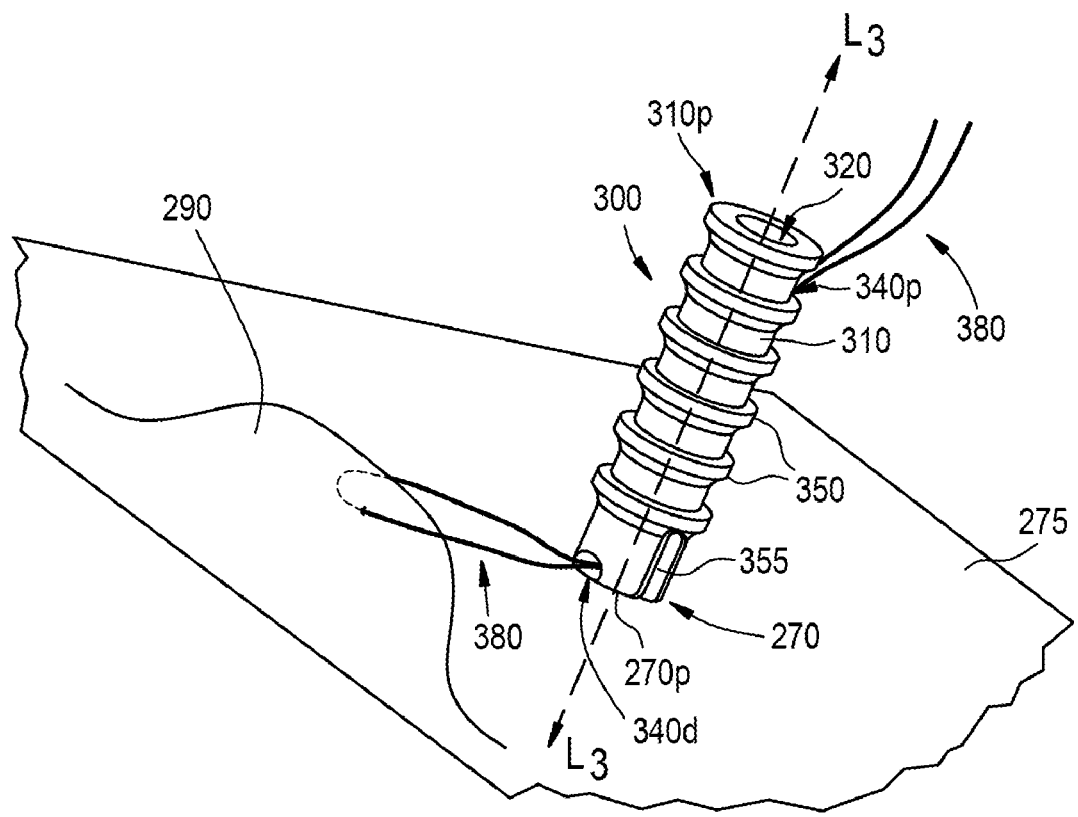
FIG. 6 is a perspective view of the suture anchor of FIG. 5A in use.

FIGS. 5A-6 illustrate still another embodiment of a suture anchor 300. The anchor 300 is similar to the previously described anchors (e.g., anchor 100, among others) in that it includes an elongate body 310 having proximal and distal ends 310p, 310d extending along a longitudinal axis $L_3$ thereof, a cutout portion 310c, a tapered distal portion 310t, a longitudinal lumen 320 extending therethrough, a suture-engaging feature 330 disposed in a distal portion of the body 310, within the lumen 320, proximal and distal side openings 340p, 340d, and bone-engaging features 350. The illustrated embodiment is included to show an additional feature disposed on the outer surface of the anchor body 310—at least one projection 355, as shown a boss feature. The projections 355 can be formed on opposed sides of the outer surface of the anchor body 310 and project radially outward from the body 310. Any number of projections can be used, and their configuration with respect to the body 310 can vary. The projections 355 have a lengthwise dimension (extending longitudinally, as defined herein) that can provide some stability as the anchor is disposed into a bone hole or bore 270 formed in bone 275.

The projections 355 are configured to facilitate suture limb 380 manipulation prior to full insertion of the suture anchor 300. For example, as illustrated in FIGS. 5A-6, the projections 355 are configured such that when a relatively planar surface disposed proximate to an entry location of a bone hole (i.e., proximal edge 270p of the bone hole 270) is engaged with a distal end of the at least one projection 355, at least a portion of the side opening 340d is disposed proximally of the proximal edge 270p of the bone hole 270 so that suture limbs 380 can pass through the side opening 340d and into the longitudinal lumen 320. As a result, the suture limbs 380 can remain slidably coupled to the suture-engaging feature 330 and be manipulated since they are not yet trapped and compressed between the bone-engaging features 350 of the body 300 and a surface (not shown) of the bone 275 that forms the bone hole 270. This configuration is achieved in the illustrated embodiment by the projections 355 being tapered radially outward as the projections 355 extend towards the proximal end 310p of the body 310. As shown, proximal ends of the projections 355 can not be tapered radially outward, i.e., the tapered configuration may not extend an entire longitudinal length of the projections 355. In some embodiments, the projections 355 can maintain at least a portion of the side opening 340d proximal to the proximal edge 270p of the bone hole 270 by providing a physical hindrance that maintains the suture anchor 300 in a partially inserted position relative to the bone hole 270. Applying additional force distally on the suture anchor 300 can overcome the physical hindrance and fully insert the suture anchor 300 to the bone hole 270.

As discussed in greater detail in other embodiments, a surgical procedure can include a step of applying tension to at least one of the two suture limbs 380 to draw the tissue 290 towards the bone 275. The projections 355 can assist in the procedure during this action because the projections 355 can help ensure that the suture limbs 380 remain slidable relative to the anchor 300, such as by way of the suture-engaging feature 330, while the anchor 300 is partially disposed within the bone hole 270. The suture limbs 380 are not yet pinched between the outer surface of the body 310 and a surface defining the bone hole 270, thus allowing for desired tensioning of the suture limbs 380 to be performed. Once the desired tensioning has been performed, the anchor 300 can be inserted into the bone hole 270 in similar manners provided for above or otherwise known to those skilled in the art. The projections 355 thus provide an impediment, but not a total barrier, to inserting the anchor 300 into the bone hole 270, with the impediment being helpful to situate the anchor 300 in the bone hole 270 while manipulating the suture limbs 380, and tissue 290 associated therewith, as desired before finally securing the location of the anchor 300 in the bone hole 270.

Figure 7A:
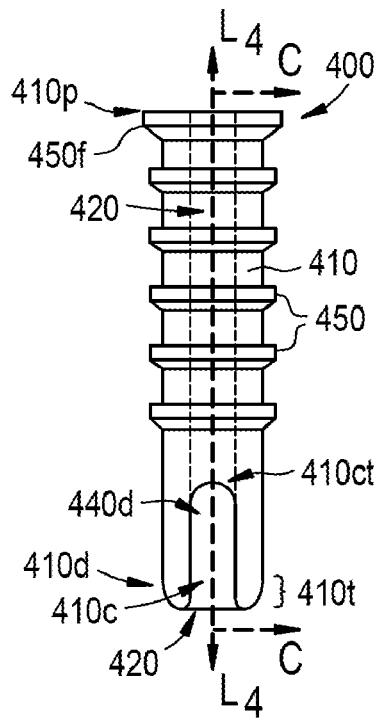
FIG. 7A is a front view of another exemplary embodiment of a suture anchor.
Figure 7B:
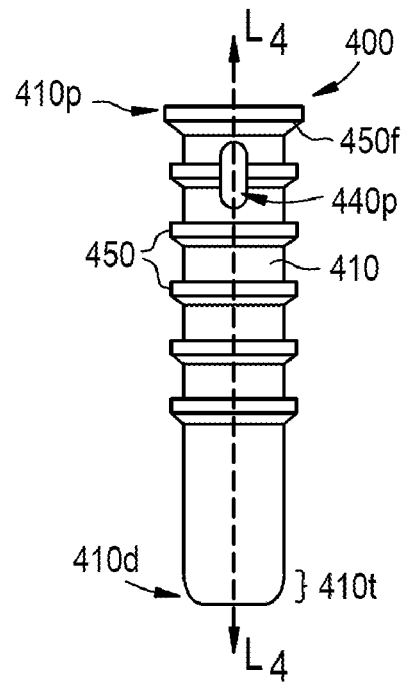
FIG. 7B is a back view of the suture anchor of FIG. 7A.
Figure 8:
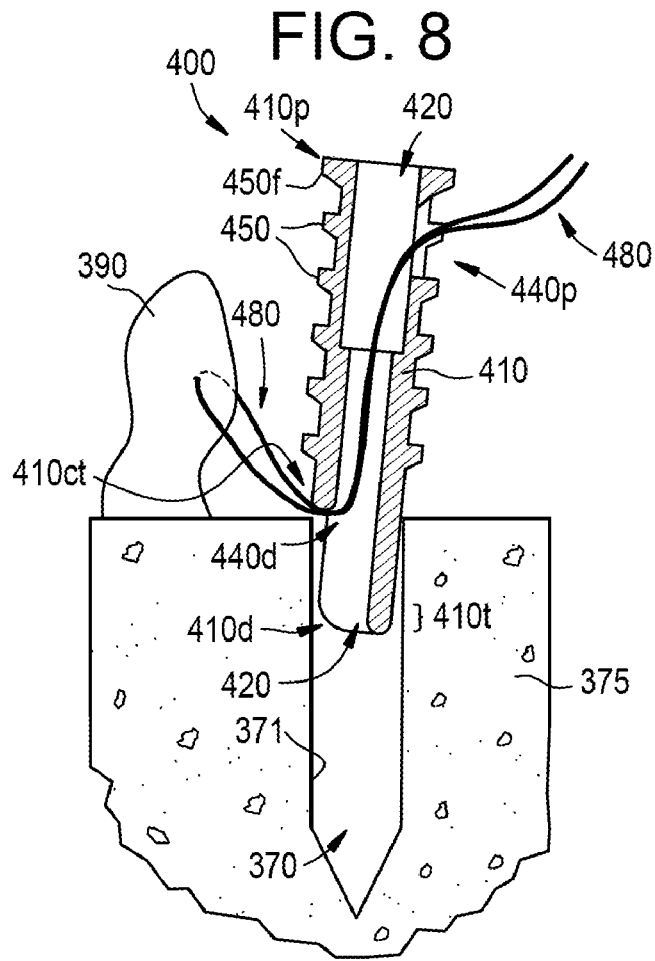
FIG. 8 is a cross-sectional view of the suture anchor of FIG. 7A taken along line C-C prior to fully inserting the anchor in a bore in a bone.

FIGS. 7A-7B and 8 illustrate another embodiment of a suture anchor 400. The anchor is similar to the previously described anchors (e.g., anchor 100, among others) in that it includes an elongate body 410 having proximal and distal ends 410p, 410d extending along a longitudinal axis $L_4$ thereof, a cutout portion 410c, a tapered distal portion 410t, a longitudinal lumen 420 extending therethrough, proximal and distal side openings 440p, 440d, and bone-engaging features 450. The illustrated embodiment is included to show at least one embodiment in which there is no separately disposed suture-engaging feature, and to illustrate a configuration in which the proximal end 410p includes a flared portion 450f in which a diameter of the bone-engaging feature(s) 450 at the proximal-most end is increased as compared to a diameter of one or more of the bone-engaging features 450 disposed more distal along the length of the anchor body 410.

As illustrated in FIG. 8, without a separately disposed suture-engaging feature, suture limbs 480 coupled to tissue 390 for drawing the tissue 390 towards bone 375 can be passed into the distal side opening 440d, engage the top surface 410ct of the cutout portion 410c, and extend proximally through the lumen 420 and out of the proximal side opening 440p (alternatively, one or more limbs can be passed through the longitudinal lumen 420 at a terminal portion of the proximal end 410p of the body 410). A top surface 410ct of the cutout portion 410c, which is also a surface that defines the distal side opening 440d, can serve as a suture-engaging feature, with the suture limbs 480 being able to slide relative to the top surface 410ct prior to full implantation of the anchor 400 into the bone 375. Like in other embodiments, as the anchor 400 becomes fully disposed in the bone hole 370 formed in the bone 375, the suture limbs 380 can become trapped between an outer surface of the body 410 and a surface 371 of the bone 375 that defines the bone hole 370. This configuration is not illustrated, but a similar such configuration is provided for with respect to a suture anchor 500 described below with respect to FIG. 10. The anchor 500 also includes a flared portion at the proximal-most end, and thus additional details about the flared portion 450f of the anchor 400 is described in greater detail below with respect to the anchor 500.

Figure 7C:
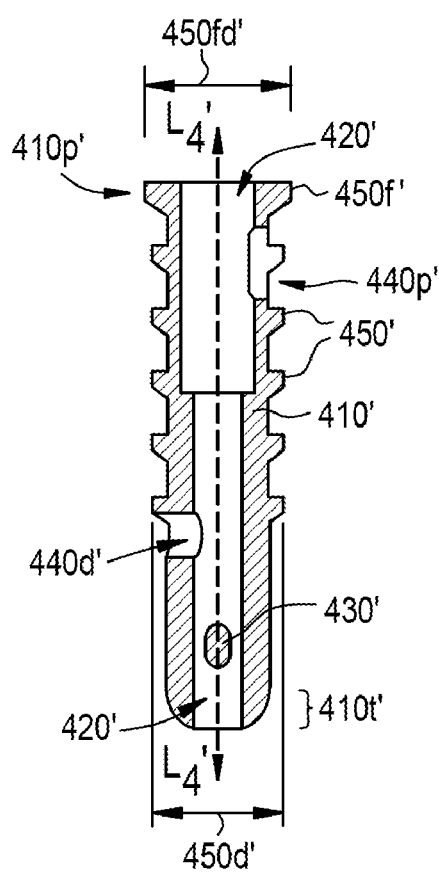
FIG. 7C is a cross-sectional front view of still another exemplary embodiment of a suture anchor, the cross-section being taken along the equivalent of line C-C of the anchor of FIG. 7A.

FIG. 7C illustrates an alternative configuration of a suture anchor 400' having a flared portion 450f'. The suture anchor 400' includes some features of the suture anchor 400, such as the flared portion 450f equivalent to the flared portion 450f, and some features of the suture anchor 200, such as a more circular-shaped distal side opening 440d' with a suture-engaging feature 430' similarly disposed as the equivalent feature 230 in the suture anchor 200. Features such as an elongate body 410' having proximal and distal ends 410p', 410d' extending along a longitudinal axis $L_4'$ thereof, a tapered distal portion 410V, a longitudinal lumen 420', the existence of proximal and distal side openings 440p', 440d', and bone-engaging features 450' are features found in the anchor 400' that are likewise found in many of the other embodiments already described above, including the anchors 400 and 200. FIG. 7C particularly labels a difference in diameters 450fd', 450d' of the flared portion 450f' and the bone-engaging features 450', respectively. In some embodiments, the flared portion 450f' can have a diameter that is approximately in the range of about 3 percent to about 20 percent greater than a diameter of more distally located bone-engaging features of the anchor, or in the range of about 3 percent to about 10 percent greater than a diameter of more distally located bone-engaging features of the anchor.

Figure 9A:
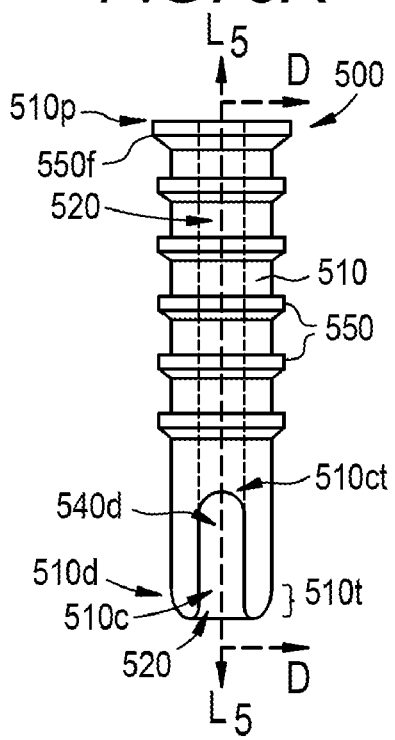
FIG. 9A is a front view of another exemplary embodiment of a suture anchor.
Figure 9B:
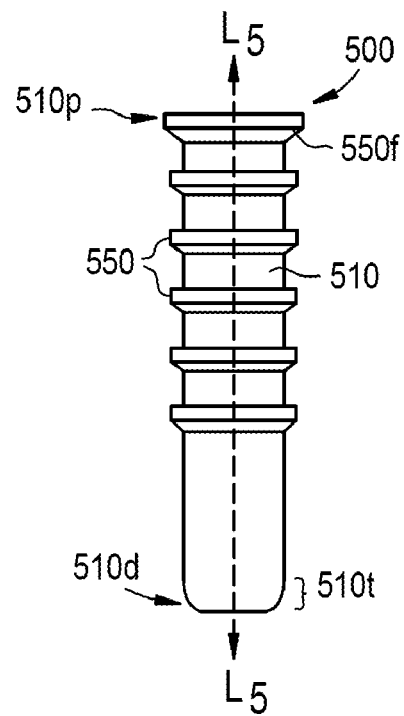
FIG. 9B is a back view of the suture anchor of FIG. 9A.
Figure 9C:
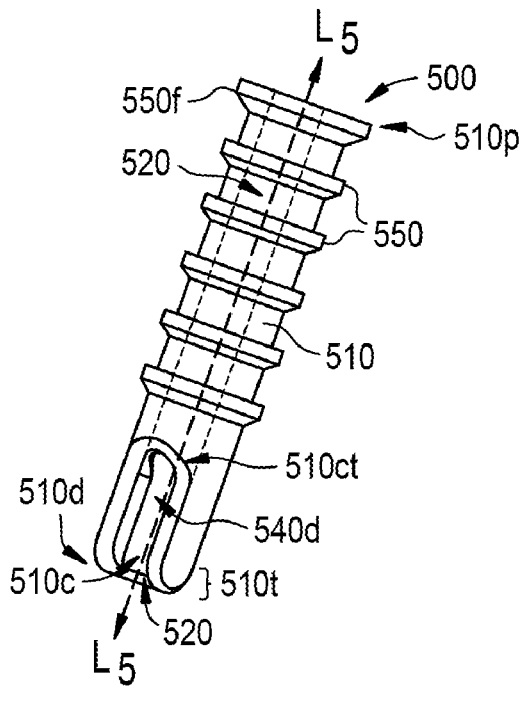
FIG. 9C is an isometric view of the suture anchor of FIG. 9A.
Figure 9D:
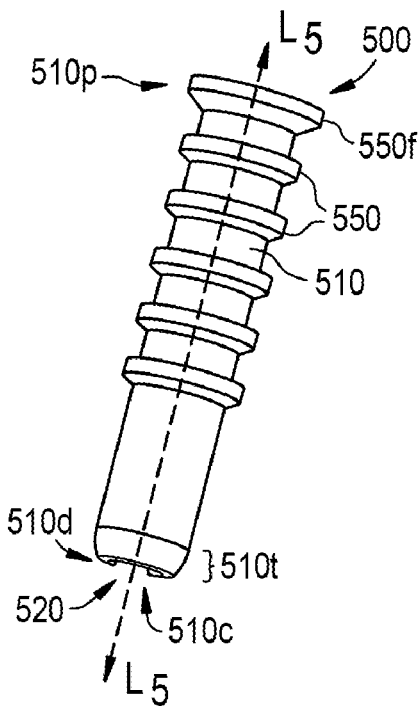
FIG. 9D is another isometric view of the suture anchor of FIG. 9A.
Figure 10:
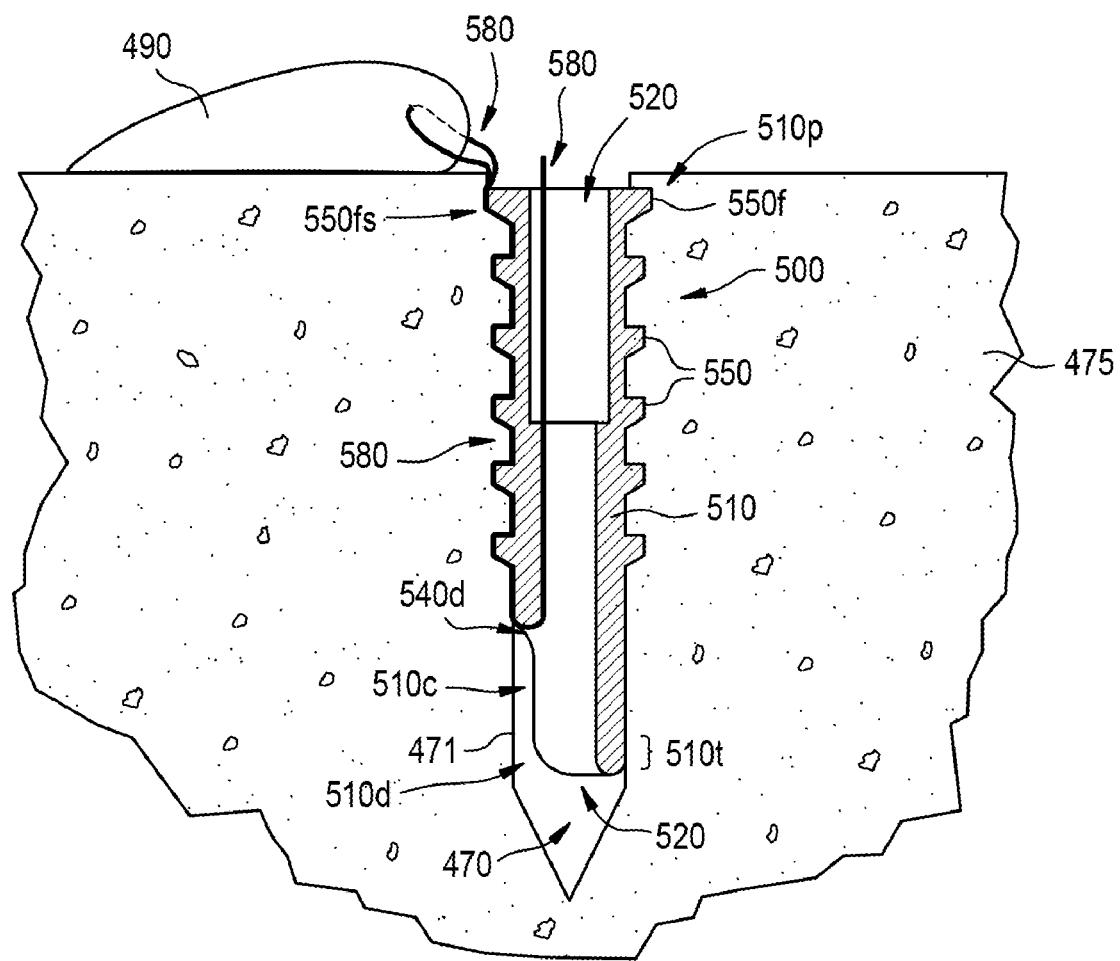
FIG. 10 is a cross-sectional view of the suture anchor of FIG. 9A taken along line D-D after fully inserting the anchor in a bore in a bone.

FIGS. 9A-10 illustrate yet another embodiment of a suture anchor 500. The anchor is again similar to the previously described anchors (e.g., anchor 100, among others) in that it includes an elongate body 510 having proximal and distal ends 510p, 510d extending along a longitudinal axis $L_5$ thereof, a cutout portion 510c, a tapered distal portion 510t, a longitudinal lumen 520 extending therethrough, a distal side opening 540d, bone-engaging-features 550, and a flared portion 550f disposed at the proximal end 510p. The illustrated embodiment is included to show an embodiment in which there is no proximal side opening, and to illustrate the impact of the flared portion 550f once the anchor 500 is implanted in a bone hole 470 formed in a bone 475. Further, similar to the anchor 400, a top surface 510ct of the cutout portion 510c, which is also a surface that defines the distal side opening 540d, can serve as a suture-engaging feature, with the suture limbs 580 being able to slide relative to the top surface 510ct prior to full implantation of the anchor 500 into the bone 475.

Because there is no proximal side opening, as shown in FIG. 10, the suture limbs 580 can extend from tissue 490, through the distal side opening 540d, engage the top surface 510ct of the cutout portion 510c, and extend proximally through the longitudinal lumen 520 until the limbs 580 exit the lumen 520 at a terminal portion of the proximal end 510p of the anchor body 510. Like in other embodiments, fully inserting anchor 500 into the bone hole 470 can trap the suture limbs 580 between an outer surface of the body 510 and the surface 471 of the bone 475 that defines the bone hole 470. However, unlike some other embodiments, the flared portion 550f can create a more secure fixation between the suture limbs 580 and the anchor 500 due, at least in part, to the increased surface area for engaging the suture limbs 580 caused by the larger diameter of the flared portion 550f, and thus an increased length of the suture limbs 580 that becomes engaged by the flared portion 550f, as shown at flared engagement section 550fs in FIG. 10. Notably, while there may be other ways to improve hold, lengthening the anchor to do so is typically not desirable because it takes up additional depth in the bone in which the implant is occurring. The use of the flared portion 550f, on the other hand, increases the compression force between the anchor 500 and the bone 475, i.e., the holding force of the anchor 500, without replacing much additional bone with the anchor.

FIGS. 11A-24 provide various suture anchor configurations by which sutures can be more easily separated and controlled. This can include configurations in which special surface features are formed in a main body of the anchor and/or in a distal portion of the anchor.

Figure 11A:
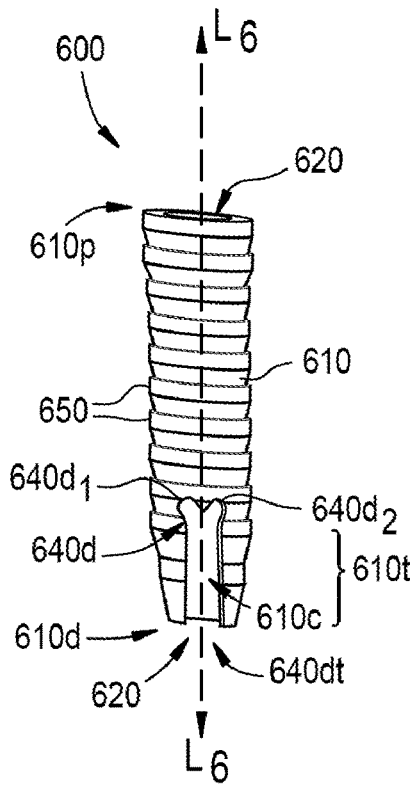
FIG. 11A is a perspective view of yet another exemplary embodiment of a suture anchor.
Figure 11B:
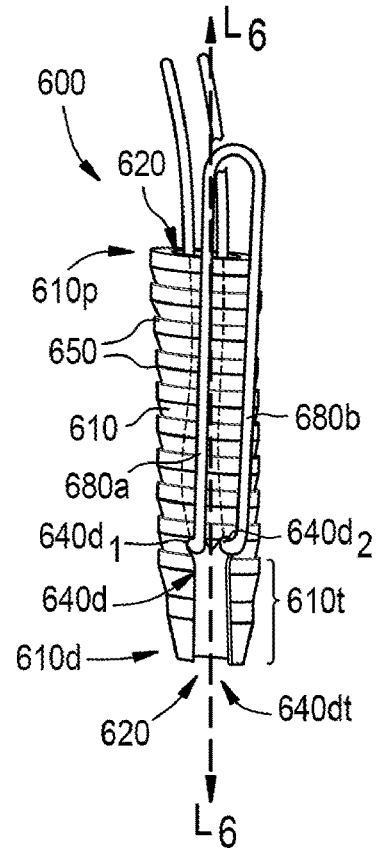
FIG. 11B is a perspective view of the suture anchor of FIG. 11A with suture limbs being slidably coupled to suture holding surfaces of the suture anchor.

FIGS. 11A-11B illustrate one exemplary embodiment of a suture anchor 600 having features designed to help control suture placement, location, and/or movement. That is not to say the previously described embodiments do not also help control suture placement, location, and/or movement, but rather, the suture anchor 600 includes a particular design in an anchor body 610 that can allow multiple suture limbs to be separated from each other for ease in identification and control while still allowing for desired slidable movement between the suture limbs and the anchor.

Some aspects of the anchor 600 are similar to the previously described anchors (e.g., anchor 100, among others) in that it includes an elongate body 610 having proximal and distal ends 610p, 610d extending along a longitudinal axis $L_6$ thereof, a cutout portion 610c, a tapered distal portion 610t, a longitudinal lumen 620 extending therethrough, a distal side opening 640d, and bone-engaging features 650. The illustrated embodiment differs from the anchor 100 at least because its distal side opening 640d is specifically designed to provide for two different surfaces $640d_1$, $640d_2$ (i.e., suture-engaging surfaces or suture holding surfaces) that can receive of hold suture limbs 680a, 680b, thus allowing those surfaces $640d_1$, $640d_2$, to separate the suture limbs 680a, 680b from each other. The surfaces $640d_1$, $640d_2$, sometimes referred to as lobes (or bifurcated lobes, where the bifurcation results from the longitudinal axis $L_6$), can be formed by a top surface 610ct of the cutout portion 610c and can provide paths for the suture limbs 680a, 680b. As shown, the cutout portion 610c can have a Y-shaped configuration with the lobes $640d_1$, $640d_2$ forming a top portion of the Y-shaped configuration (i.e., the "arms" of the Y-shaped configuration) and a stem of the Y-shaped configuration extending from the lobes $640d_1$, $640d_2$ and to the distal end 610d of the body 610. Alternative shapes and/or configurations of surfaces of a distal side opening are provided with respect to later described embodiments, the different shapes and/or configurations providing alternative holding surfaces, forces, and paths for suture limbs associated therewith.

More particularly with regards to the anchor 600 of FIGS. 11A-11B, the surfaces $640d_1$, $640d_2$ are disposed on opposed sides of the longitudinal axis $L_6$. As shown, the surfaces $640d_1$, $640d_2$ are curved and symmetrical with respect to each other vis-à-vis the longitudinal axis $L_6$, forming a scalloped configuration or scalloped portion of the distal side opening 640. As a result, at least two suture paths are formed, one each on opposed sides of the longitudinal axis $L_6$. As shown in FIG. 11B, two suture limbs 680a, 680b can be separated such that one suture limb, as shown limb 680a, engages the surface $640d_1$ and the other suture limb, as shown limb 680b, engages the surface $640d_2$. This allows the limbs 680a, 680b to be easily separated a distance apart, identified, and held with respect to the anchor 600. One advantage of such a configuration is improved ease of manipulation of the suture limbs 680a, 680b when placing the suture limbs 680a, 680b through the distal side opening 640d and through the longitudinal lumen 620, as both limbs 680a, 680b can be inserted through the same terminal end 640dt of the side opening 640d, which is also the terminal end of the lumen 620. The discrete lobes $640d_1$, $640d_2$ that keep the two suture limbs 680a, 680b a distance apart can reduce the likelihood of crossing portions of the suture limbs that are being secured between the suture anchor and the bone hole during a surgery. The illustrated configuration, as well as others, can help prevent overlap of suture limbs. Suture limb overlap can have a negative impact on the ability of the anchor to hold the suture at a desired location.

Figure 12A:
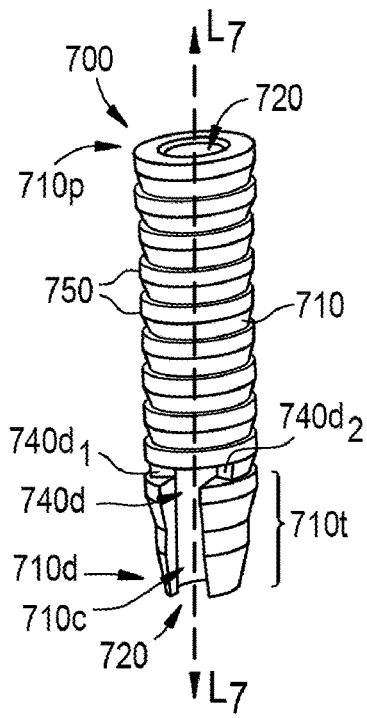
FIG. 12A is a perspective view of another exemplary embodiment of a suture anchor.
Figure 12B:
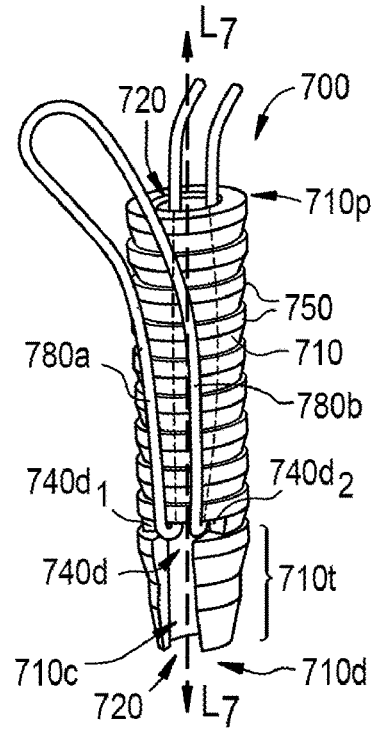
FIG. 12B is a perspective view of the suture anchor of FIG. 12A with suture limbs being slidably coupled to suture holding surfaces of the suture anchor.

FIGS. 12A-12B illustrate another embodiment of a suture anchor 700. The anchor 700 is similar to the previously described anchors (e.g., anchor 600, among others) in that it includes an elongate body 710 having proximal and distal ends 710p, 710d extending along a longitudinal axis $L_7$ thereof, a cutout portion 710c, a tapered distal portion 710t, a longitudinal lumen 720 extending therethrough, a distal side opening 740d, and bone-engaging features 750. The illustrated embodiment is included to show an alternative configuration of a cutout portion. As shown, the cutout portion 710c includes surfaces $740d_1$, $740d_2$ that have more of a rectangular-shaped or window configuration as compared to the surfaces $640d_1$, $640d_2$. The surfaces $740d_1$, $740d_2$ can serve as suture-engaging surfaces for the anchor 700 in the absence of a separately located suture-engaging feature (e.g., suture-engaging features 130, 330, 430'). More particularly, as shown, the surfaces $740d_1$, $740d_2$ are disposed substantially transverse to the longitudinal axis $L_7$ of the anchor body 710. The use and purpose of the surfaces $740d_1$, $740d_2$ are similar to the surfaces $640d_1$, $640d_2$. Accordingly, as shown in FIG. 12B, a first suture limb 780a can be coupled to or otherwise associated with the surface $740d_1$, and a second suture limb 780b can be coupled to or otherwise associated with the surface $740d_2$, thereby keeping the two suture limbs 780a, 780b separated from each other. In the illustrated embodiment the two surfaces $740d_1$, $740d_2$ are on opposed sides of the longitudinal axis $L_7$, but other configurations are possible.

Figure 13A:
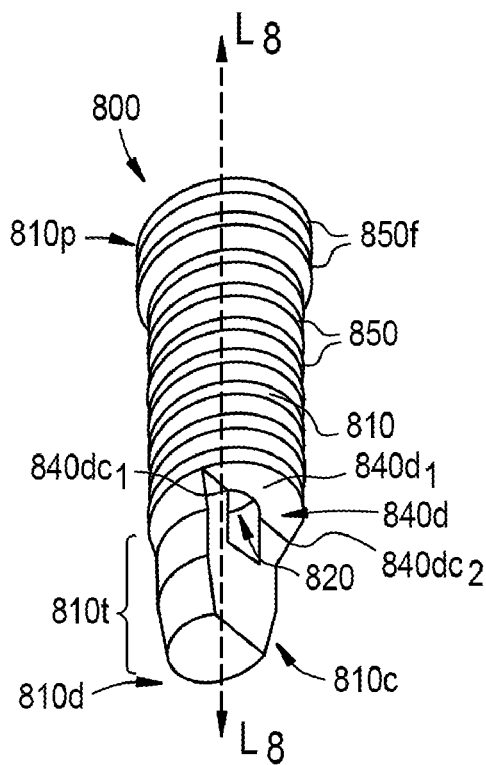
FIG. 13A is a perspective view of still another exemplary embodiment of a suture anchor.
Figure 13B:
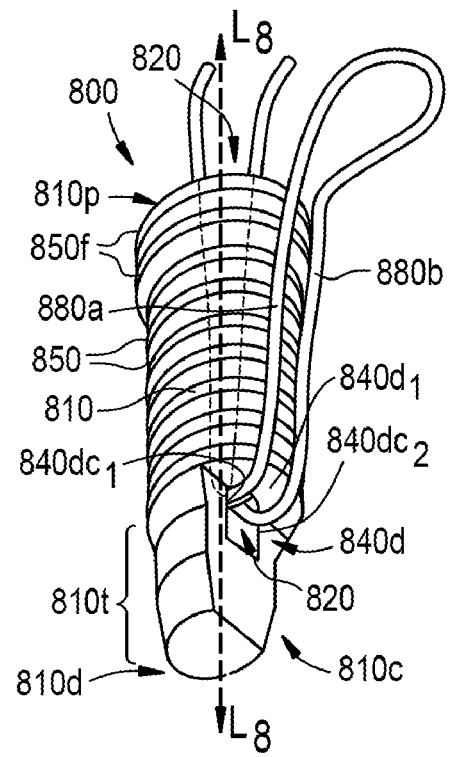
FIG. 13B is a perspective view of the suture anchor of FIG. 13A with suture limbs being slidably coupled to suture holding surfaces of the suture anchor.

FIGS. 13A-13B illustrate still another embodiment of a suture anchor 800. The anchor 800 is similar to the previously described anchors (e.g., anchor 600, among others) in that it includes an elongate body 810 having proximal and distal ends 810p, 810d extending along a longitudinal axis $L_8$ thereof, a cutout portion 810c, a tapered distal portion 810t, a longitudinal lumen 820 extending therethrough, a distal side opening 840d, and bone-engaging features 850. Similar to the anchors 400, 400', and 500, it also includes flared portions 850f that can serve similar purposes as the flared portions 450f, 450f, and 550f. The illustrated embodiment is included to show still another alternative configuration of a cutout portion. As shown, the cutout portion 810c includes a shelf $840d_1$ that can engage suture limbs in the absence of a separately disposed suture-engaging feature. A surface of the shelf $840d_1$ can be substantially transverse to the longitudinal axis $L_8$, allowing, as shown in FIG. 13B, for suture limbs 880a, 880b to engage with the shelf $840d_1$ just as suture limbs engage with other surfaces formed by a cutout portion in other embodiments provided for herein. The illustrated configuration can help provide for separation of the suture limbs 880a 880b at corners $840dc_1$, $840dc_2$ of the shelf $840d_1$ disposed on opposed side of the longitudinal axis $L_8$. In some embodiments, the corners $840dc_1$, $840dc_2$ can include divots, grooves, scallops, or other configurations that can allow the suture limbs 880a, 880b to be more easily separated from each other and held at or proximate to their desired locations at the corners $840dc_1$, $840dc_2$.

Figure 14A:
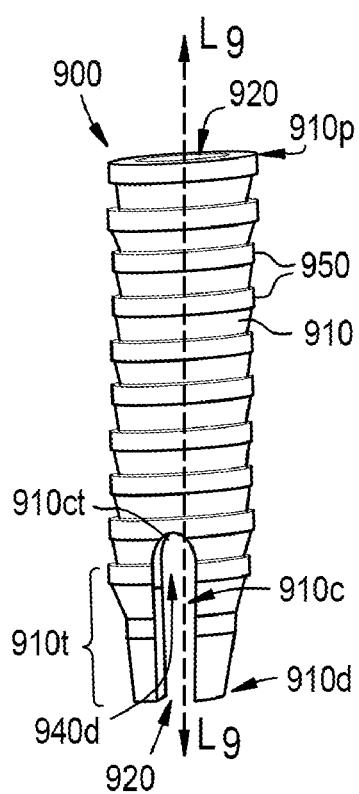
FIG. 14A is a perspective view of another exemplary embodiment of a suture anchor.
Figure 14B:
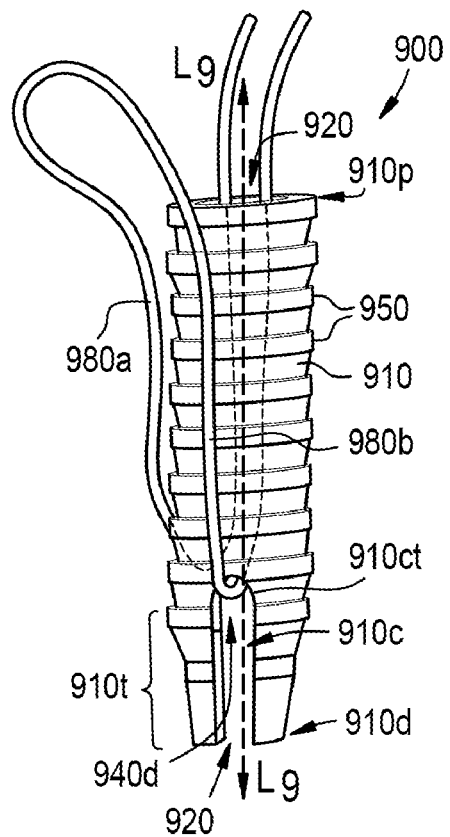
FIG. 14B is a perspective view of the suture anchor of FIG. 14A with suture limbs being slidably coupled to suture holding surfaces of the suture anchor.

FIGS. 14A-14B illustrate another embodiment of a suture anchor 900. The anchor 900 is similar to the previously described anchors (e.g., anchor 600, among others) in that it includes an elongate body 910 having proximal and distal ends 910p, 910d extending along a longitudinal axis $L_9$ thereof, a cutout portion 910c, a tapered distal portion 910t, a longitudinal lumen 920 extending therethrough, a distal side opening 940d, and bone-engaging features 950. The illustrated embodiment is included to show another alternative configuration of a cutout portion. More specifically, the cut out portion 910c extends fully through a volume of the anchor 900, resulting in a distal side opening 940d that extends through an entire diameter of the anchor 900. As shown, a shape of the distal side opening 940d on opposed surfaces of the anchor body 910 is symmetrical, although other configurations are possible, such as a configuration in which various shapes of the cutout portions and distal openings provided for herein are mixed and matched and/or other shapes and configurations are utilized to form the distal side opening 940d. As described in earlier embodiments, a top surface 910ct of the cutout portion 910c can be configured in a manner that further assists in separating and/or holding suture limbs 980a, 980b separate from each other.

Figure 15A:
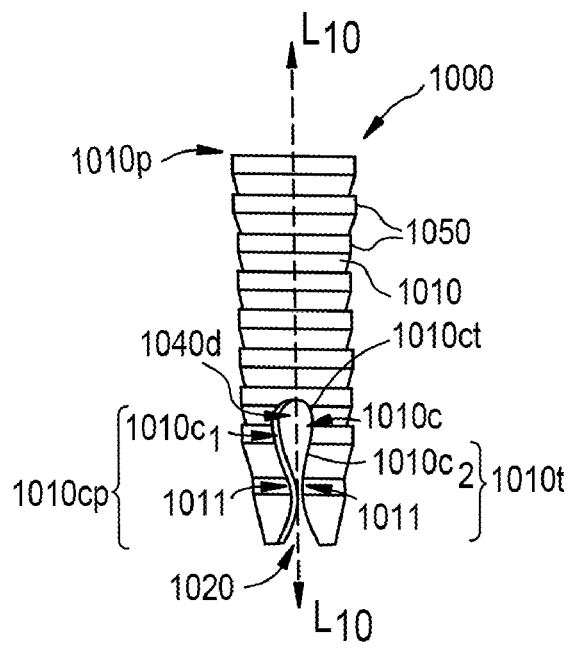
FIG. 15A is a perspective view of yet another exemplary embodiment of a suture anchor.
Figure 15B:
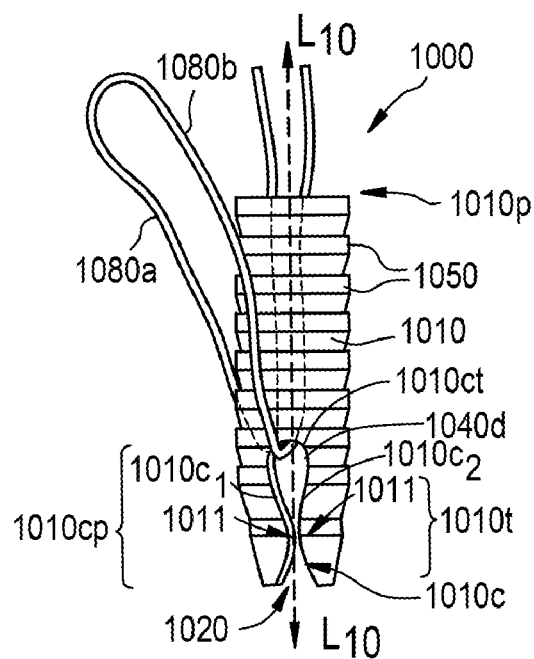
FIG. 15B is a perspective view of the suture anchor of FIG. 15A with suture limbs being slidably coupled to suture holding surfaces of the suture anchor.

FIGS. 15A-15B illustrate yet another embodiment of a suture anchor 1000. The anchor 1000 is similar to the previously described anchors (e.g., anchor 600, among others) in that it includes an elongate body 1010 having proximal and distal ends 1010p, 1010d extending along a longitudinal axis $L_{10}$ thereof, a cutout portion 1010c, a tapered distal portion 1010t, a longitudinal lumen 1020 extending therethrough, a distal side opening 1040d, and bone-engaging features 1050. The illustrated embodiment is included to show yet another alternative configuration of a cutout portion. More specifically, the cutout portion 1010c includes opposed longitudinal surfaces $1010c_1$, $1010c_2$ that have a changing diameter between a top surface 1010ct of the cutout portion 1010c and the distal end 1010d. This causes the distal side opening 1040d to become pinched or narrowed, up to a narrowest location 1011, and then expand back out again as the surfaces $1010c_1$, $1010c_2$ reach the distal end 1010d. As shown, the opposed longitudinal surfaces $1010c_1$, $1010c_2$ are symmetrically opposed with respect to the longitudinal axis $L_{10}$. Similar to the cutout portion 910c, the cutout portion 1010c can extend fully through a volume of the anchor 1000, resulting in a distal side opening 1040d that extends through an entire diameter of the anchor 1000. Accordingly, the opposed longitudinal surfaces $1010c_1$, $1010c_2$ of the cutout portion 1010c are formed on opposed sides of the anchor body 1010. As shown in FIG. 15B, the configuration of the anchor 1000 can enhance retention of the suture limbs 1180a, 1180b with respect to the distal side opening 1040d.

Figure 16A:
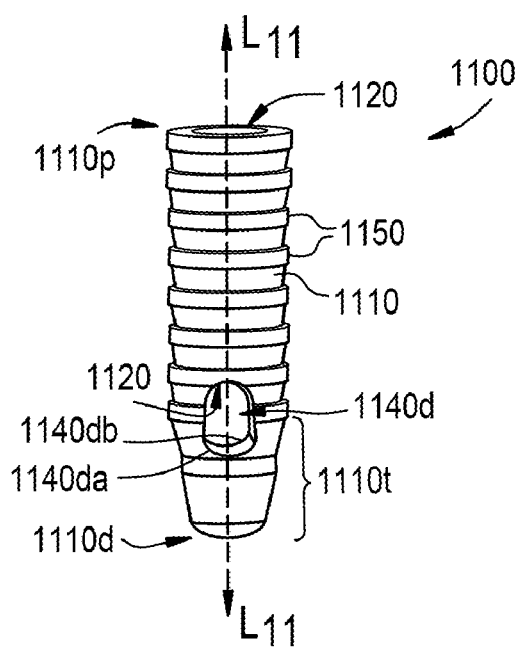
FIG. 16A is a perspective view of another exemplary embodiment of a suture anchor.
Figure 16B:
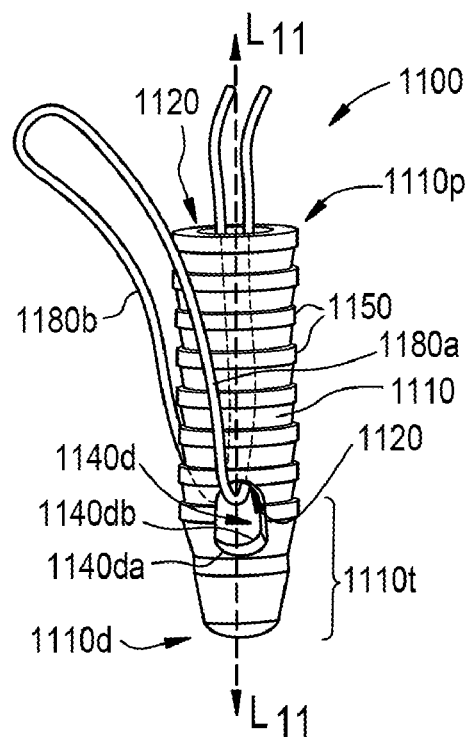
FIG. 16B is a perspective view of the suture anchor of FIG. 16A with suture limbs being slidably coupled to suture holding surfaces of the suture anchor.

FIGS. 16A-16B illustrate another embodiment of a suture anchor 1100. The anchor 1100 is similar to the previously described anchors (e.g., anchor 200, among others) in that it includes an elongate body 1110 having proximal and distal ends 1110p, 1110d extending along a longitudinal axis $L_{11}$ thereof, a tapered distal portion 1110t, a longitudinal lumen 1120 extending therethrough, a distal side opening 1140d, and bone-engaging features 1150. The illustrated embodiment is included to show a configuration in which the distal side opening 1140d extends through to an opposed side of the anchor body 1110 but does not extend all the way down to the distal end 1110d. As shown, the distal side opening 1140d has a substantially elliptical shape or cross-section and extends from one side of the anchor body 1110 to an opposed side of the anchor body 1110. As shown in FIG. 16B, two suture limbs 1180a, 1180b can be disposed through opposed sides 1140da, 1140db of the distal side opening 1140d, respectively, and passed up through the longitudinal lumen 1120. Like in other embodiments, in alternative embodiments, one or more other side openings, such as a proximal side opening (not shown), can be included and one or both suture limbs 1180a, 1180b can be passed through such an opening in lieu of, or even in addition to, passing through the longitudinal lumen 1120 at the proximal end 1110p of the body 1110.

Figure 17:
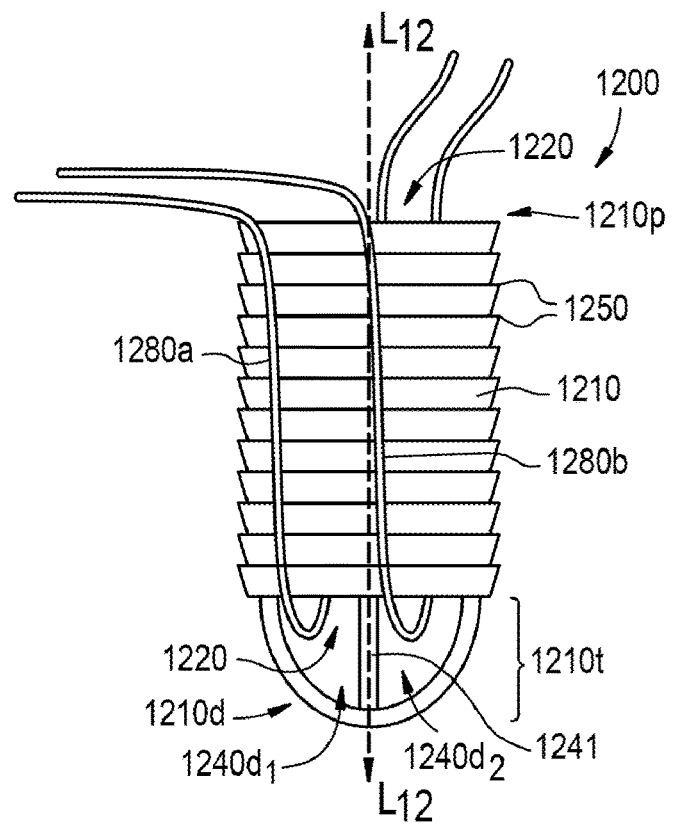
FIG. 17 is a schematic side view of still another exemplary embodiment of a suture anchor.

FIG. 17 illustrates still another embodiment of a suture anchor 1200. The anchor 1200 is similar to the previously described anchors (e.g., anchor 100, among others) in that it includes an elongate body 1210 having proximal and distal ends 1210p, 1210d extending along a longitudinal axis Lie thereof, a tapered distal portion 1210t, a longitudinal lumen 1220 extending therethrough, and bone-engaging features 1250. Somewhat akin to the anchor 600 of FIGS. 11A-11B, the illustrated embodiment is included to show an anchor 1200 that includes two separately formed surfaces for purposes of being able to differentiate, hold, or otherwise separately identify two or more suture limbs. More particularly, as shown the anchor 1200 includes two distal side openings $1240d_1$, $1240d_2$ that are separated by a longitudinal wall 1241 extending to the distal end 1210d, thereby forming bifurcated passageways within the anchor 1200. In the illustrated embodiment the longitudinal wall 1241 extends along the longitudinal axis $L_{12}$, although a person skilled in the art will recognize it can be disposed in other locations such that it does not necessarily create two equally sized distal side openings $1240d_1$, $1240d_2$ and/or more than one such wall can be provided for in other embodiments. The longitudinal wall 1241 can, but does not have to, extend into some or all of the longitudinal lumen 1200. This configuration allows for clear delineation of locations through which suture limbs 1280a, 1280b can be passed, with in the illustrated embodiment the suture limb 1280a passing through the distal side opening $1240d_1$ and up through the longitudinal lumen 1220 before exiting the lumen 1220 at the proximal end 1210p, and the suture limb 1280b passing through the distal side opening $1240d_2$ and up through the longitudinal lumen 1220 before also existing the lumen 1220 at the proximal end 1210p. As with other embodiments, in alternative configurations one or both suture limbs 1280a, 1280b can exit the longitudinal lumen 1220 through one or more other side openings (not shown) formed in the anchor body 1210.

Figure 18:
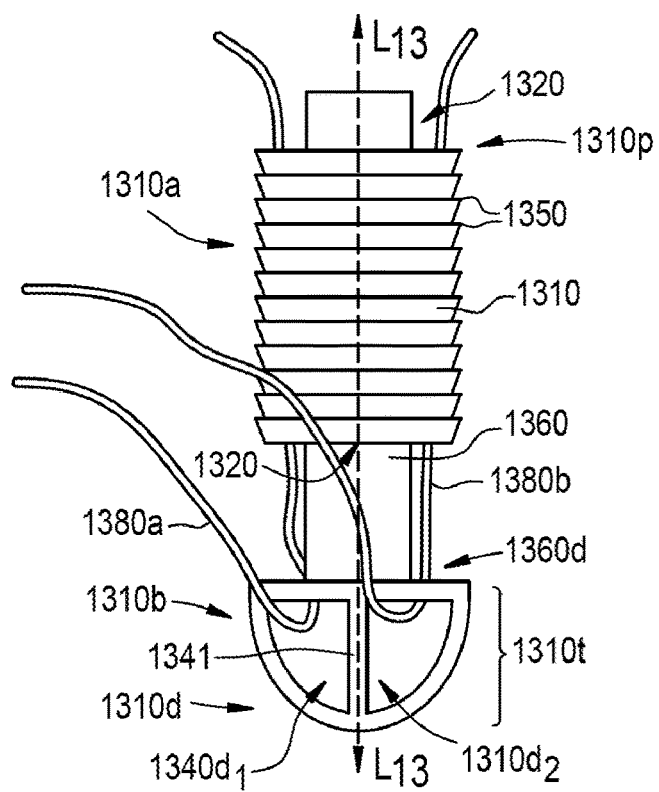
FIG. 18 is a schematic side view of another exemplary embodiment of a suture anchor.

FIG. 18 illustrates another embodiment of a suture anchor 1300. The anchor 1300 is similar to the previously described anchors (e.g., anchor 1200, among others) in that it includes an elongate body 1310 having proximal and distal ends 1310p, 1310d extending along a longitudinal axis Lia thereof, a tapered distal portion 1310t, a longitudinal lumen 1320 extending therethrough, two distal side openings $1340d_1$, $1340d_2$, a longitudinal wall 1341 extending to the distal end 1310d and separating the two distal side openings $1340d_1$, $1340d_2$, and bone-engaging features 1350. The illustrated embodiment is included to show a configuration in which the elongate body 1310 can be separated into multiple parts, as shown a proximal portion or proximal main member 1310a and a distal portion or distal tip member 1310b. As shown, an insertion rod 1360 can be provided to assist in implanting the suture anchor 1300 during a surgical procedure. The combination of the anchor 1300 and rod 1360 can be considered a suture anchor insertion assembly. In the illustrated embodiment the distal portion 1310b of the anchor body 1310 can be mounted to a distal end 1360d of the insertion rod and the proximal portion 1310a of the anchor body 1310 can be slidably disposed on the rod 1360 so it can translate along the rod 1360 to selectively couple to the distal portion 1310b. Any number of known techniques for mating one component to another can be used to mate the proximal portion 1310a with the distal portion 1310b. One benefit provided by this configuration is that it can be easier to control suture tension, as compared to other embodiments provided for herein that do not separate fixation into two pieces or components.

FIGS. 19A and 19B illustrate two embodiments of suture anchor insertion assemblies, the assemblies including both two further embodiments of a suture anchor 1400, 1400' and an insertion rod 1460, 1460'. Each anchor 1400, 1400' is similar to the previously described anchors (e.g., anchor 1300, among others) in that each includes an elongate body 1410, 1410' having proximal and distal ends 1410p, 1410d, 1410p', 1410d' extending along a longitudinal axis $L_{14}$, $L_{14}$' thereof, a tapered distal portion 1410t, 1410t', a longitudinal lumen 1420, 1420' extending therethrough, bone-engaging features 1450, 1450', and separable proximal portions or proximal main members 1410a, 1410a' and distal portions or distal tip members 1410b, 1410b' of the elongate bodies 1410, 1410'. In the illustrated embodiment, the longitudinal lumen 1420, 1420' extends through the proximal main member 1410a, 1410a' but not the distal tip member 1410b, 1410b', although in other embodiments the longitudinal lumen 1420, 1420' may extend through part or all of the distal tip member 1410b, 1410b'. The anchor 1400 is also similar to the anchor 1300 in that its distal portion 1410b includes two distal side openings $1440d_1$, $1440d_2$, while the anchor 1400' is similar to the anchor 600 of FIGS. 11A-11B in that it includes one distal side opening 1440d' having different surfaces $1440d_1$', $1440d_2$' (i.e., suture-engaging surfaces) formed therein in a Y-shaped configuration. Accordingly, similar to the surfaces $640d_1$', $640d_2$' of the anchor 600, the surfaces $1440d_1$', $1440d_2$' can be identified as lobes or scallops of the single opening 1440d'. In both embodiments, the respective distal side openings $1440d_1$, $1440d_2$ and surfaces $1440d_1$', $1440d_2$' of the distal side opening 1440d' are symmetrically disposed on opposed sides of the longitudinal axis $L_{14}$, $L_{14}$'.

As shown, the distal tip members 1410b, 1410b' can be removably mated to distal ends 1460d, 1460d' of the insertion rods 1460, 1460' and the proximal main members 1410a, 1410a' can be slidably disposed along the rods 1460, 1460', although a person skilled in the art will appreciate that other configurations for inserting separable portions of an anchor body can be used without departing from the spirit of the present disclosure. The insertion rod 1460, 1460' can be decoupled from the distal tip member 1410b, 1410b' during a surgical procedure, such as after the distal tip member 1410b, 1410b' has been positioned at a desired location in a bore formed in bone and/or after the proximal main member 1410a, 1410a' has been inserted and secured to the distal tip member 1410b, 1410b'. Notably, at least because embodiments like the assembly of FIGS. 19A-19B are schematic illustrations, a person skilled in the art will appreciate that components including but not limited to the insertion rods 1460, 1460' can have many different configurations, including larger and smaller diameters, shapes, lengths, etc.

The bone-engaging features 1450 of FIG. 19A are different than the bone-engaging features 1450' of FIG. 19B because the bone-engaging features 1450 include a single, corkscrew-shaped thread extending radially around the outer surface of the elongate body 1410, as compared to the protrusions or ribs that form the bone-engaging features 1450'. Either way, just like the bone-engaging features of the various embodiments provided for herein, the bone-engaging features 1450, 1450' help facilitate secure engagement of the proximal main member 1410a, 1410a' within a bone hole or bore formed in bone. As described elsewhere herein, suture limbs 1480a, 1480b, 1480a', 1480b' passed into the distal side openings $1440d_1$, $1440d_2$, 1440d', through the longitudinal lumen 1420, 1420', and out of the lumen 1120, 1120' either at the proximal end 1410p, 1410p' of the body 1410, 1410' or at one or more other side openings (not shown) can be captured between the bone-engaging features 1450, 1450' and a bone surface that forms a bore in bone, respectively. The bone-engaging features 1450, 1450' can provide a frictional force on suture limbs 1480a, 1480b, 1480a', 1480b' configured to be secured at a surgical location by the anchors 1400, 1400', and can provide additional surface area by which the limbs 1480a, 1480b, 1480a', 1480b' can be engaged when the anchors 1400, 1400' are implanted into a bore formed in bone. Similar to the suture anchor 1300 of FIG. 18, one benefit provided by the configuration of the suture anchor 1400, 1400' of FIGS. 19A and 19B is that it can be easier to control suture tension, as compared to other embodiments provided for herein that do not separate fixation into two pieces or components.

Figure 20A:
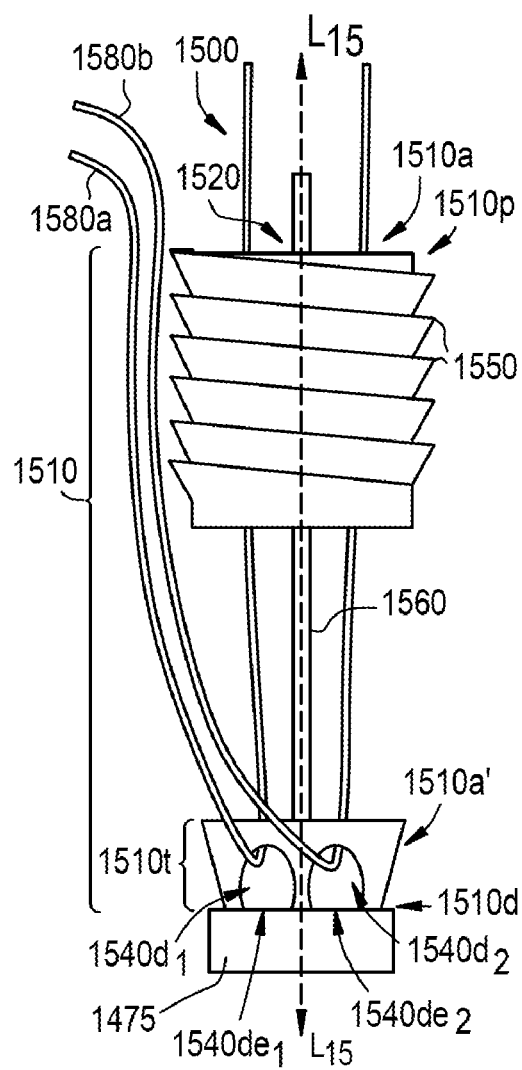
FIG. 20A is a schematic side view of still another exemplary embodiment of a suture anchor.
Figure 20B:
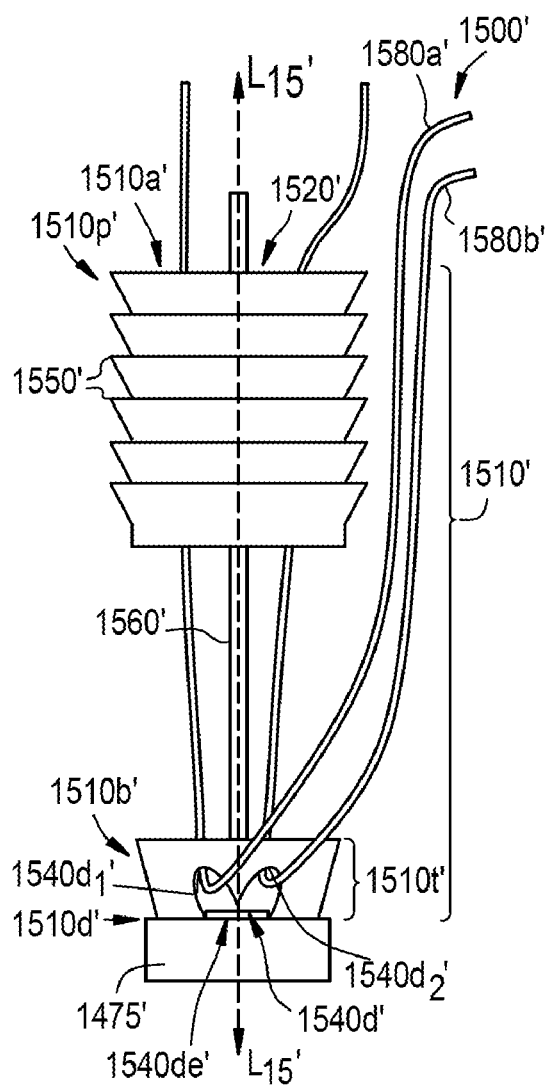
FIG. 20B is a schematic side view of another exemplary embodiment of a suture anchor.

FIGS. 20A and 20B illustrate two further embodiments of suture anchor insertion assemblies that include two still further embodiments of a suture anchor 1500, 1500' and an insertion rod 1560, 1560'. Each anchor 1500, 1500' is similar to the previously described anchors (e.g., anchors 1400, 1400', among others) in that each includes an elongate body 1510, 1510' having proximal and distal ends $1510p$, $1510d$, $1510p'$, $1510d'$ extending along a longitudinal axis $L_{15}$, $L_{15}'$ thereof, a tapered distal portion $1510t$, $1510t'$, a longitudinal lumen 1520, 1520' extending therethrough, bone-engaging features 1550, 1550', and a separable proximal portion or proximal main member 1510a, 1510a' and distal portion or distal tip member 1510b, 1510b' of the elongate body 1510, 1510'. Similar to the longitudinal lumen 1420, 1420', the longitudinal lumen 1520, 1520' extends through the proximal main member 1510a, 1510a' and may or may not extend into at least some portion of the distal tip member 1510b, 1510b'. The configurations of the distal side openings $1540d_1$, $1540d_2$, $1540d'$ is also similar, except that the openings themselves are not fully enclosed and can be described as being grooves. The openings $1540d_1$, $1540d_2$, $1540d'$ have distal ends $1540de_1$, $1540de_2$, $1540de'$ that are themselves open, allowing for suture limbs 1580a, 1580b, 1580a', 1580b' to be passed through the open distal ends, such as by moving them substantially parallel to the longitudinal axis $L_{15}$, $L_{15}'$, and into contact with the grooves $1540d_1$, $1540d_2$, $1540d'$. In the illustrated embodiment, a schematic illustration of a bone 1475, 1475' is provided to illustrate how the distal tip member 1510b, 1510b' can engage bone to close the openings $1540d_1$, $1540d_2$, $1540d'$. In use, however, the openings $1540d_1$, $1540d_2$, $1540d'$ can remain open at the distal end, for example if appropriate tension is applied to suture limbs 1580a, 1580b, 1580a', 1580b' associate therewith such that there is no risk to the suture limbs 1580a, 1580b, 1580a', 1580b' falling out or otherwise away from the openings $1540d_1$, $1540d_2$, $1540d'$, and more particularly surfaces $1540d_1{}^1$, $1540d_2{}'$ of the opening $1540d'$. Similar to the suture anchor 1300 of FIG. 18 and suture anchor 1400, 1400' of FIGS. 19A and 19B, one benefit provided by the configuration of the suture anchor 1500, 1500' of FIGS. 20A and 20B is that it can be easier to control suture tension, as compared to other embodiments provided for herein that do not separate fixation into two pieces or components.

Figure 21:
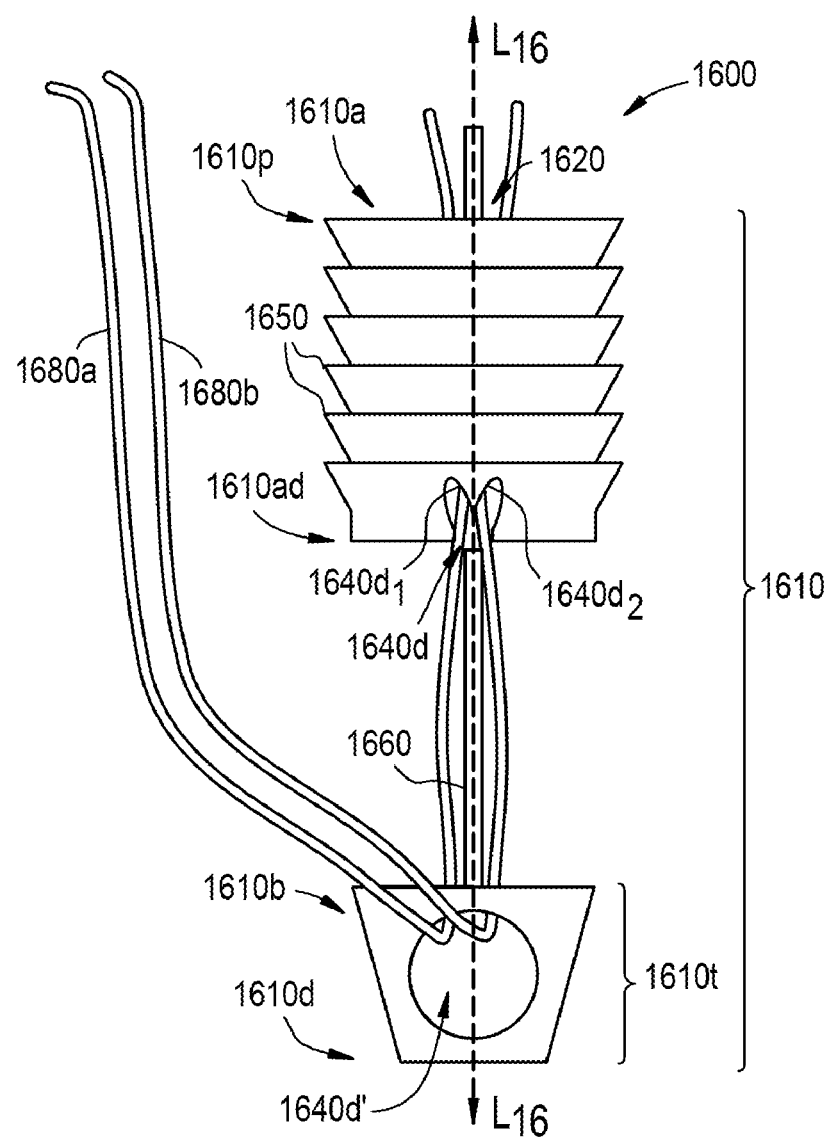
FIG. 21 is a schematic side view of yet another exemplary embodiment of a suture anchor.

FIG. 21 illustrates still another embodiment of a suture anchor insertion assembly that includes a suture anchor 1600 and an insertion rod 1660. The anchor 1600 is similar to previously described anchors (e.g., anchors 1500, 1500', among others) in that it includes an elongate body 1610 having proximal and distal ends $1610p$, $1610d$ extending along a longitudinal axis Lib thereof, a tapered distal portion $1610t$, a longitudinal lumen 1620 extending therethrough, bone-engaging features 1650, and a separable proximal portion or proximal main member 1610a and distal portion or distal tip member 1610b of the elongate body 1610. The illustrated embodiment is included to show one non-limiting embodiment in which features designed to more easily separate or hold suture limbs, or identify suture limbs, are formed in another location beyond a distal tip member when the anchor includes multiple components. More particularly, in the illustrated embodiment, the equivalent of grooves $1540d_1'$, $1540d_2'$ are formed in the proximal main member 1610a. As shown, surfaces $1640d_1$, $1640d_2$ of a distal side opening $1640d$ can be formed in a distal end $1610ad$ of the proximal main member 1610a, with the surfaces $1640d_1$, $1640d_2$ forming lobes or scallops configured to receive and hold suture limbs 1680a, 1680b. In the illustrated embodiment, the portion of the rod 1660 that passes through the opening $1640d$ is removed to make it easier to see the distal side opening $1640d$. Further, the distal tip member 1610b can include one or more distal side openings as well, as shown a second distal side opening $1640d'$. Accordingly, in some instances, such as the illustrated embodiment, suture limbs 1680a, 1680b can be passed through the second distal side opening $1640d'$ of the distal tip member 1610b, across the surfaces $1640d_1$, $1640d_2$ formed in the proximal main member 1610a, and through at least a portion of the longitudinal lumen 1620 before exiting the lumen 1620 at the proximal end $1610p$ of the elongate body 1610 or through another side opening (not shown). In other embodiments, suture limbs 1680a, 1680b may not pass through any portion of the distal tip member 1610b. Yet again, similar to the suture anchor 1300 of FIG. 18, the suture anchor 1400, 1400' of FIGS. 19A and 19B, and the suture anchor 1500, 1500' of FIGS. 20A and 20B, one benefit provided by the configuration of the suture anchor 1600 of FIG. 21 is that it can be easier to control suture tension, as compared to other embodiments provided for herein that do not separate fixation into two pieces or components.

While the present disclosures already provide for some non-limiting examples of the disclosed anchors and assemblies used in conjunction with a surgical procedure, and additional procedures will be well understood by a person skilled in the art based on the features and descriptions of the various anchor embodiments, FIGS. 22A-22B provide a further non-limiting example of a surgical procedure that utilizes the devices and assemblies disclosed herein, and more particularly the assembly that includes the anchor 1400 and rod 1460 of FIG. 19A.

The process can include coupling the suture limbs 1480a, 1480b to tissue 1390, such as by passing the limbs 1480a, 1480b through the tissue 1390 and/or wrapping the limbs 1480a, 1480b around the tissue 1390. The limbs 1480a, 1480b can then be passed through the respective distal side openings $1440d_1$, $1440d_2$ formed in the distal tip member 1410b. The limbs 1480a, 1480b can be passed up through the longitudinal lumen 1420 formed in the proximal main member 1410a, the limbs 1480a, 1480b exiting the proximal main member 1410a at the proximal end $1410p$ of the elongate body 1410. In embodiments that include other side openings, one or more of the limbs 1480a, 1480b can pass out of the side openings in lieu of or in addition to passing out of the proximal end $1410p$ of the body 1410. The distal tip member 1410b can be disposed in a bore or hole 1370 formed in a bone 1375 to which the tissue 1390 is to be attached. This can be achieved, for example, by using the rod 1460 to insert the distal tip member 1410b to the surgical site.

After the distal tip member 1410b is positioned in its desired location, such as when the distal end $1410d$ of the body 1410 contacts a distal terminal end of the bone hole 1370, the proximal main member 1410a can be slid down the rod 1460 so that it abuts the distal tip member 1410b, as illustrated in FIG. 22B. They can be fixedly coupled together using any techniques known to those skilled in the art if desired. As the proximal main member 1410*a* enters the bone hole 1370, at least a portion of the suture limbs 1480*a*, 1480*b* can be engaged by both the bone-engaging features 1450 and a surface 1371 of the bone 1375 that defines the hole 1370. This occurs in FIG. 22 to the viewer in a three-dimensional abstraction of the figure towards the viewer, similar to the way the bone-engaging features 150 of the anchor 100 in FIG. 2B impinge the suture limbs 180 between them and the surface 71 of the bone 75 that defines the bone hole 70. The insertion of the proximal main member 1410*a* towards the distal tip member 1410*b* can result in a locked configuration in which the suture limbs 1480*a*, 1480*b* are locked into place with respect to the anchor 1400 and the bone 1375, in turn locking the tissue 1390 in place with respect to the anchor 1400 and the bone 1375. This may occur after the proximal main and distal tip members 1410*a*, 1410*b* are connected, or at some point before if the proximal main member 1410*a* is sufficiently deep into the bone hole 1370. The rod 1460 can be decoupled from the distal tip member 1410*b* after the proximal main member 1410*a* is positioned as desired. In other embodiments, the rod 1460 may not be used to assist with inserting the proximal main member 1410*a*, in which case it can be removed prior to distally advancing the proximal main member 1410*a* towards the distal tip member 1410*b*.

The suture limbs 1480*a*, 1480*b* can be manipulated to move draw the tissue 1390 towards the anchor 1400, and thus the bone 1375. Alternatively, or additionally, the suture limbs 1480*a*, 1480*b* can be tensioned sufficiently such that advancing the proximal main member 1410*a* distally towards the distal tip member 1410*b* can cause the tissue 1390 to be drawn towards the bone 1375. Further, while the illustrated embodiment provides for associating the suture limbs 1480*a*, 1480*b* with the anchor 1400 prior to insertion, the limbs 1480*a*, 1480*b* can be associated with at least some portions of the anchor 1400 after at least a portion of the anchor 1400 has been implanted in the bore 1370. For example, the suture limbs 1480*a*, 1480*b* can be coupled to the distal side openings 1440*d*$_1$, 1440*d*$_2$ prior to insertion of the distal tip member 1410*b* in the bore 1370, but passed through the longitudinal lumen 1420 after the distal tip member 1410*b* is inserted in the bore 1370. A person skilled in the art will appreciate the order of most of the steps provided for in conjunction with the surgical methods described herein can be performed in different orders without departing from the spirit of the present disclosure.

Figure 23:
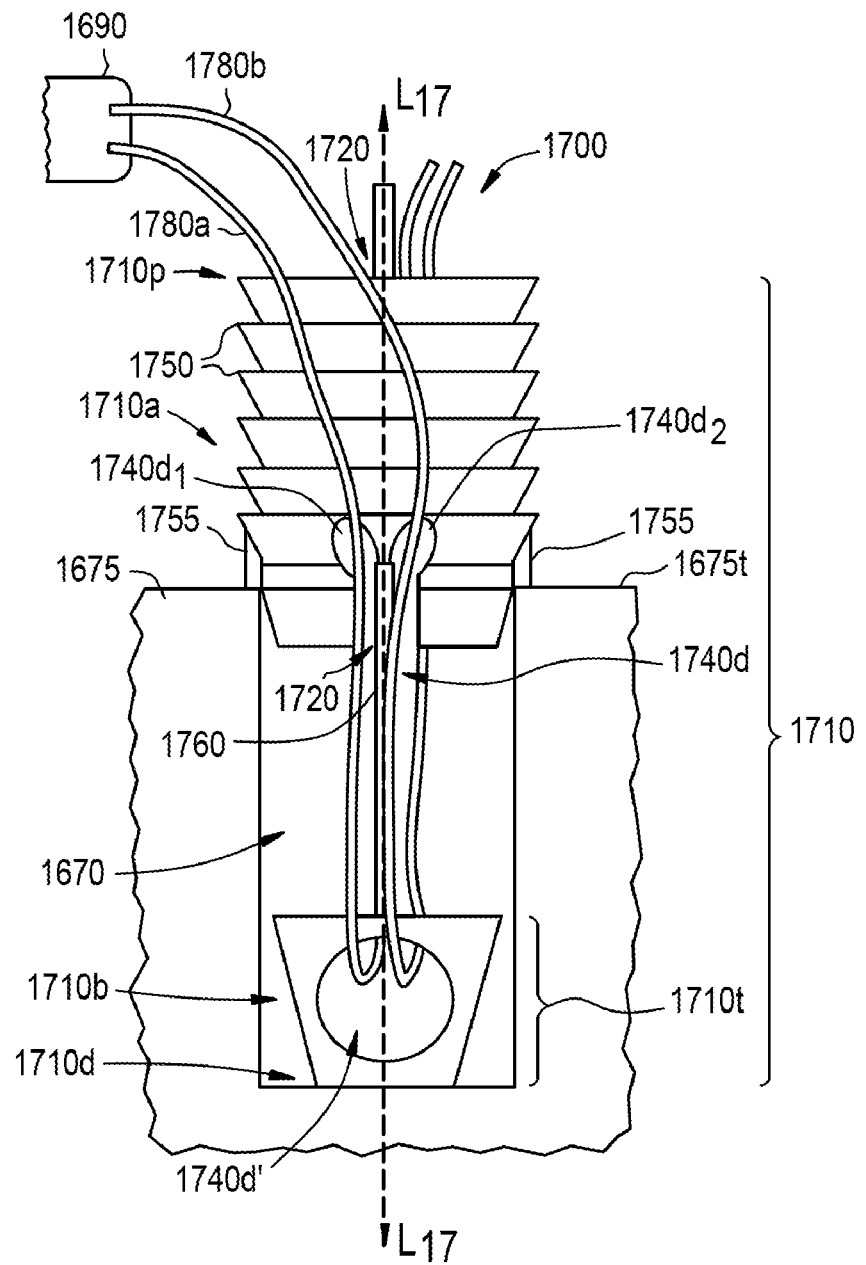
FIG. 23 is a schematic side view of another exemplary embodiment of a suture anchor in use.

FIG. 23 illustrates another non-limiting embodiment of a suture anchor insertion assembly, and a method of using the same. The suture anchor insertion assembly includes a suture anchor 1700 and an insertion rod 1760. The anchor 1700 is similar to previously describe anchors (e.g., anchor 1600, among others) in that it includes an elongate body 1710 having proximal and distal ends 1710*p*, 1710*d* extending along a longitudinal axis L$_{17}$ thereof, a tapered distal portion 1710*t*, a longitudinal lumen 1720 extending therethrough, bone-engaging features 1750, a separable proximal portion or proximal main member 1710*a* and distal portion or distal tip member 1710*b* of the elongate body 1710, a distal side opening 1740*d* formed in the proximal main member 1710*a* and having surfaces 1740*d*$_1$, 1740*d*$_2$, and a second distal side opening 1740*d'* formed in the distal tip member 1710*b*. The illustrated embodiment is included to show a second embodiment in which projections 1755 are formed on an outer surface of the anchor body 1710—more particularly on the proximal main member 1710*a*—for reasons similar to the projections 355 of the anchor 300 illustrated in FIGS. 5A-6. As shown the projections 1755 are formed on opposed surfaces of the body 1710. The projections 1755 can engage a top surface 1675*t* of the bone 1675, thereby allowing manipulation of suture limbs 1780*a*, 1780*b* with respect to the anchor 1700 and tissue 1690 associated therewith. More particularly, the suture limbs 1780*a*, 1780*b* can be slid through the second distal side opening 1740*d'*, against the surfaces 1740*d*$_1$, 1740*d*$_2$ of the distal side opening 1740*d*, and through the longitudinal lumen 1720 of the body 1710 prior to imparting sufficient force to overcome the obstacle provided by the projections 1755. Even after the proximal main member 1710*a* is advanced towards the distal tip member 1710*b* and into a bore 1670 formed in the bone 1675, some manipulation of the suture limbs 1780*a*, 1780*b* with respect to the anchor 1700 may be possible.

The various embodiments of suture anchors and insertion assemblies provided for herein allow for improved suture tensioning, and further, allow for the resultant suture retention forces associated with the same to be maximized. This is due, at least in part, to the various configurations of side openings (e.g., the proximal and distal side openings 140*p*, 140*d*, among others), suture-engaging features (e.g., the suture-engaging feature 130, among others), and bone-engaging features (e.g., the bone-engaging features 150, among others), and the way suture limbs interact with the same during a surgical procedure. Once implantation occurs, the associated suture limbs are also securely held by virtue of being trapped by the outer surface of the anchors and the surfaces of bone that define the bone hole in which the anchor is implanted. The various embodiments also make implantation procedures easier, including for the aforementioned reasons related to tensioning, and also because of the ease of holding, separating, and/or identifying sutures, for example by way of particularly configured distal side openings (e.g., the distal side opening 640*d*, among others).

One skilled in the art will appreciate further features and advantages of the present disclosure based on the above-described embodiments. Accordingly, the disclosure and associated invention is not to be limited by what has been particularly shown and described, except as indicated by the appended claims. For example, to the extent the disclosures provided for herein describe devices and methods used in conjunction with soft tissue repairs, a person having skill in the art would be able to apply these disclosures to other surgical procedures that require suture retention to the bone, and with other anatomies and in other locations of the body without departing from the spirit of the present disclosure. Further, although the devices and methods provided for herein are generally directed to surgical techniques, at least some of the devices and methods can be used in applications outside of the surgical field. One skilled in the art will also appreciate that various features and/or elements of the different embodiments of the disclosure can be combined in a variety of ways. Unless clearly physically impossible to achieve, one or more features from one embodiment can be combined with one or more features of one or more other embodiments. Further, to the extent particular embodiments illustrate side openings that extend only partially through a volume of the anchor, or fully through the volume of the anchor, a person skilled in the art will recognize that such configurations can be modified to allow for the openings to extend fully through the volume or anchor, or just partially through the volume of the anchor, as desired.

What is claimed is:

1. A surgical method of affixing tissue to a bone, the method comprising:
coupling a suture to tissue such that two suture limbs extend from the tissue;
passing each of the two suture limbs into and through a first opening formed by a cutout in a sidewall of a distal tip portion of a suture anchor, at least a portion of a longitudinal lumen of the suture anchor being in communication with the first opening to receive each of the two suture limbs therethrough, the longitudinal lumen having one or more suture engagement features such that the two suture limbs are slidably disposed with respect to the one or more suture engagement features;
extending at least one limb of the two suture limbs through the portion of the longitudinal lumen and out of the longitudinal lumen through a second opening formed in a sidewall of a proximal portion of the suture anchor, the second opening being located proximal to the first opening and on a side of a central longitudinal axis that extends centrally through the longitudinal lumen of the suture anchor that is opposed to a side from the profile view in which the first opening is formed such that the at least one limb extends into and out of the longitudinal lumen on opposite sides of the central longitudinal axis, the at least one limb extending proximally through the longitudinal lumen as it extends between the first and second openings;
inserting the suture anchor into a bore formed in bone; and
applying tension to at least one of the two suture limbs to draw the tissue towards the bone; and
advancing the suture anchor distally into the bore to lock a location of the two suture limbs, and thus the tissue coupled to the bone, at a location relative to the bone.

2. The surgical method of claim 1,
wherein each of the two suture limbs being slidably disposed with respect to the one or more suture engagement features of the distal tip portion further comprises engaging the at least one limb with a first surface of the first opening and engaging a second limb of the two suture limbs with a second surface of the first opening.

3. The surgical method of claim 1,
wherein the action of each of the two suture limbs being slidably disposed with respect to the one or more suture engagement features of the distal tip portion occurs prior to the action of passing the two suture limbs from the one or more suture engagement features of the distal tip portion into and through at least a portion of the proximal portion of the suture anchor.

4. The method of claim 3, wherein the second opening is below and proximate to a proximal end of the suture anchor.

5. The surgical method of claim 1,
wherein the proximal portion of the suture anchor is part of a proximal main member and the distal portion is part of a distal tip member, the method further comprising moving the proximal main member towards the bore formed in the bone until one or more protrusions disposed on the proximal main member engage the bone proximate to the bore such that the proximal main member cannot advance further towards the bore without application of an additional amount of force to the proximal main member, the engagement of the one or more protrusions with the bone providing a gap between the proximal main member and a proximal edge of the bore to accommodate movement of the two suture limbs with respect to first and second surfaces of the first and second openings, respectively, and
wherein advancing the suture anchor distally into the bore to lock a location of the two suture limbs further comprises advancing the proximal main member distally towards the distal tip member to lock the location of the two suture limbs and results in elimination of the gap.

6. The method of claim 1, wherein the first opening is defined by a top surface of the one or more suture engagement features and a proximal-most surface of the cutout in the sidewall of the distal tip portion.

7. The method of claim 1, wherein the at least one limb exits the longitudinal lumen prior to reaching a proximal end of the suture anchor.

8. The method of claim 7, wherein at least a portion of the at least one limb is trapped by a proximal member of the suture anchor between the bore and an outer surface of the suture anchor.

9. The method of claim 8, wherein at least a portion of the two suture limbs is trapped between the bore and the outer surface of the suture anchor.

10. The method of claim 9, wherein the portion of the two suture limbs trapped between the bore and the outer surface of the suture anchor are trapped on opposite sides of the central longitudinal axis that extends centrally through the longitudinal lumen from the at least one limb trapped by the proximal member of the suture anchor.

11. The method of claim 9, wherein the two suture limbs are trapped across a substantial length of the outer surface of the bone anchor.

12. The method of claim 11, wherein the two suture limbs extend along the outer surface of the suture anchor from the tissue to the first opening.

13. The method of claim 8, wherein the at least one limb engages one or more bone-engaging features on the outer surface to affix the suture limbs relative to the bone by enhancing the retention force to secure the limbs.

14. The method of claim 1, wherein the one or more suture engagement features includes a rod-shaped member extending substantially transverse to the central longitudinal axis of the suture anchor from one side of an internal surface of the longitudinal lumen to an opposite side of the longitudinal lumen.

15. The method of claim 1, wherein the two suture limbs are disposed onto, around, or otherwise associated with the one or more suture engagement features.

16. The method of claim 1, wherein the bore is pre-drilled or pre-existing prior to insertion of the anchor therethrough.

17. The method of claim 1, further comprising passing a second limb of the two suture limbs through the second opening.

18. The method of claim 1, wherein coupling the suture to tissue further comprises wrapping one or both suture limbs around tissue.

19. The method of claim 1, further comprising passing a second limb of the two suture limbs out of the longitudinal lumen at a terminal portion of a proximal end of the suture anchor.

20. The method of claim 1, further comprising sliding the suture limbs relative to the suture anchor prior to inserting the suture anchor into the bore.

* * * * *